(12) United States Patent
Langhorn et al.

(10) Patent No.: US 11,491,043 B2
(45) Date of Patent: Nov. 8, 2022

(54) BODY SIDE MEMBER OF AN OSTOMY APPLIANCE

(71) Applicant: Coloplast A/S, Humlebaek (DK)

(72) Inventors: Philip Holler Langhorn, Hilleroed (DK); Birthe Vestbo Andersen, Espergaerde (DK); Lars Stendevad Windeballe, Virum (DK); Kristoffer Hansen, Naerum (DK); Kasper Friis, Copenhagen (DK); Anders Ravn Joergensen, Copenhagen (DK); Richard Morgan Hickmott, Helsingoer (DK)

(73) Assignee: Coloplast A/S, Humlebaek (DK)

( * ) Notice: Subject to any disclaimer, the term of this patent is extended or adjusted under 35 U.S.C. 154(b) by 378 days.

(21) Appl. No.: 16/498,409

(22) PCT Filed: Apr. 9, 2018

(86) PCT No.: PCT/DK2018/050068
§ 371 (c)(1),
(2) Date: Sep. 27, 2019

(87) PCT Pub. No.: WO2018/188706
PCT Pub. Date: Oct. 18, 2018

(65) Prior Publication Data
US 2021/0085510 A1    Mar. 25, 2021

(30) Foreign Application Priority Data
Apr. 10, 2017 (DK) .......................... PA 2017 70258

(51) Int. Cl.
*A61F 5/443* (2006.01)
*A61F 5/448* (2006.01)

(52) U.S. Cl.
CPC .............. *A61F 5/443* (2013.01); *A61F 5/448* (2013.01)

(58) Field of Classification Search
CPC ........ A61F 5/445; A61F 5/443; A61F 5/4404; A61L 24/0073; A61L 2400/14
See application file for complete search history.

(56) References Cited

U.S. PATENT DOCUMENTS

| 3,081,771 A | * | 3/1963 | Clarence, I | ............. A61F 5/443 604/344 |
| 4,753,703 A | * | 6/1988 | Jensen | ..................... A61F 5/443 414/791.2 |
| 4,793,337 A | * | 12/1988 | Freeman | ................. A61L 15/58 442/151 |
| 5,051,259 A | * | 9/1991 | Olsen | .................. A61F 13/0213 428/355 R |

(Continued)

FOREIGN PATENT DOCUMENTS

| CN | 1233945 A | 11/1999 |
| CN | 1427703 A | 7/2003 |

(Continued)

*Primary Examiner* — Guy K Townsend
(74) *Attorney, Agent, or Firm* — Coloplast Corp., Coloplast A/S; Nick Baumann

(57) ABSTRACT

A body side member of an ostomy appliance having a distal surface with one or more pockets holding a manipulable material and allowing the manipulable material to be shifted between a first position and a second position in the pocket in use of the body side member around a stoma of a user.

22 Claims, 9 Drawing Sheets

(56) References Cited

U.S. PATENT DOCUMENTS

| | | | | |
|---|---|---|---|---|
| 5,074,852 A * | 12/1991 | Castellana | ............... | A61F 5/443 604/336 |
| 5,591,820 A * | 1/1997 | Kydonieus | ............. | C08G 18/73 528/905 |
| 5,714,543 A * | 2/1998 | Shah | ........................ | C08L 29/00 525/123 |
| 5,912,059 A * | 6/1999 | Jones | ...................... | A61F 5/443 428/35.5 |
| 6,332,879 B1 * | 12/2001 | Nielsen | .................... | A61F 5/443 604/336 |
| 6,764,474 B2 | 7/2004 | Nielsen et al. | | |
| 6,869,422 B2 * | 3/2005 | Fenton | ..................... | A61F 5/445 604/338 |
| 7,347,844 B2 * | 3/2008 | Cline | ........................ | A61F 5/448 604/338 |
| 7,857,796 B2 * | 12/2010 | Cline | ........................ | A61F 5/448 604/277 |
| 7,858,836 B2 * | 12/2010 | Sambasivam | ............ | A61L 15/40 523/111 |
| 8,439,883 B1 * | 5/2013 | Johnsen | ................... | A61F 5/448 604/338 |
| 2002/0088080 A1 * | 7/2002 | Fenton | ..................... | A61F 5/445 604/338 |
| 2003/0004477 A1 * | 1/2003 | Nielsen | .................... | A61F 5/448 604/336 |
| 2003/0093042 A1 * | 5/2003 | Leisner | .................... | A61F 5/448 604/338 |
| 2004/0193122 A1 * | 9/2004 | Cline | ........................ | A61F 5/448 604/332 |
| 2004/0223944 A1 * | 11/2004 | Capelli | ................. | A61K 47/585 424/618 |
| 2004/0230170 A1 * | 11/2004 | Fenton | ..................... | A61F 5/445 604/336 |
| 2006/0141016 A1 * | 6/2006 | Sambasivam | ............ | A61P 17/00 424/773 |
| 2007/0179461 A1 * | 8/2007 | Sambasivam | ........... | C09J 183/04 604/336 |
| 2008/0119804 A1 * | 5/2008 | Cline | ....................... | A61F 5/445 604/338 |
| 2008/0319368 A1 * | 12/2008 | Lykke | ................... | A61F 13/025 602/57 |
| 2009/0311307 A1 * | 12/2009 | Lykke | ...................... | B05D 3/00 424/443 |
| 2010/0168693 A1 * | 7/2010 | Edvardsen | ............... | A61F 5/451 604/355 |
| 2011/0213322 A1 * | 9/2011 | Cramer | .................... | A61F 5/443 604/332 |
| 2013/0096522 A1 * | 4/2013 | Svensby | ................... | A61F 5/445 604/336 |
| 2013/0123678 A1 * | 5/2013 | Carty | ................... | A61F 13/0253 602/54 |
| 2015/0018788 A1 * | 1/2015 | Pham | ...................... | B32B 27/08 428/518 |
| 2015/0284597 A1 * | 10/2015 | Carty | ......................... | C09J 7/38 206/229 |
| 2015/0359656 A1 * | 12/2015 | Hansen | .................... | A61F 5/445 604/344 |
| 2016/0235582 A1 * | 8/2016 | Moavenian | ............ | A61F 5/448 |
| 2016/0302959 A1 * | 10/2016 | Kavanagh | ................ | A61F 5/443 |
| 2017/0095431 A1 * | 4/2017 | Andrews | ................ | A61K 9/7084 |
| 2020/0046541 A1 * | 2/2020 | Sund | ....................... | A61F 5/445 |

FOREIGN PATENT DOCUMENTS

| | | | | |
|---|---|---|---|---|
| CN | 102753122 A | | 10/2012 | |
| EP | 0686381 A | * | 12/1995 | ............. A61F 5/443 |
| EP | 0686381 A1 | | 12/1995 | |
| RU | 2582426 C2 | | 4/2016 | |
| RU | 2595010 C2 | | 8/2016 | |
| WO | 2016162038 A1 | | 10/2016 | |
| WO | WO-2016162038 A1 | * | 10/2016 | ............. A61F 5/445 |
| WO | 2017059868 A1 | | 4/2017 | |
| WO | WO-2017059868 A1 | * | 4/2017 | ........... A61F 5/4404 |

\* cited by examiner

BODY SIDE MEMBER OF AN OSTOMY APPLIANCE

BACKGROUND

Stomal output often contains body fluids and visceral contents that are aggressive to both the skin of a user and to ostomy devices, in particular these have a detrimental effect on the efficiency and integrity of the adhesive materials that are applied to attach the ostomy device to the user's skin surface. Some ostomists may choose or have to wear their device for prolonged periods of time. For users in general, and particularly for these ostomists safe, reliable and efficient ostomy devices are highly desirable. Numerous attempts have been made to provide ostomy devices to meet the such demands, e.g. the demand of prolonged wear time, but the provision of sufficient efficiency to achieve a satisfactory long wear time of ostomy devices continues to be an unmet need.

Ostomists and health care professionals alike would welcome improvements in ostomy devices to better meet such demands.

SUMMARY

The present disclosure provides aspects of a body side member of an ostomy appliance according to the appended claims.

BRIEF DESCRIPTION OF THE DRAWINGS

The accompanying drawings are included to provide a further understanding of embodiments and are incorporated in and constitute a part of this specification. The drawings illustrate embodiments and together with the description serve to explain principles of embodiments. Other embodiments and many of the intended advantages of embodiments will be readily appreciated as they become better understood by reference to the following detailed description. The elements of the drawings are not necessarily to scale relative to each other. Like reference numerals designate corresponding similar parts.

DETAILED DESCRIPTION

Figure 1:
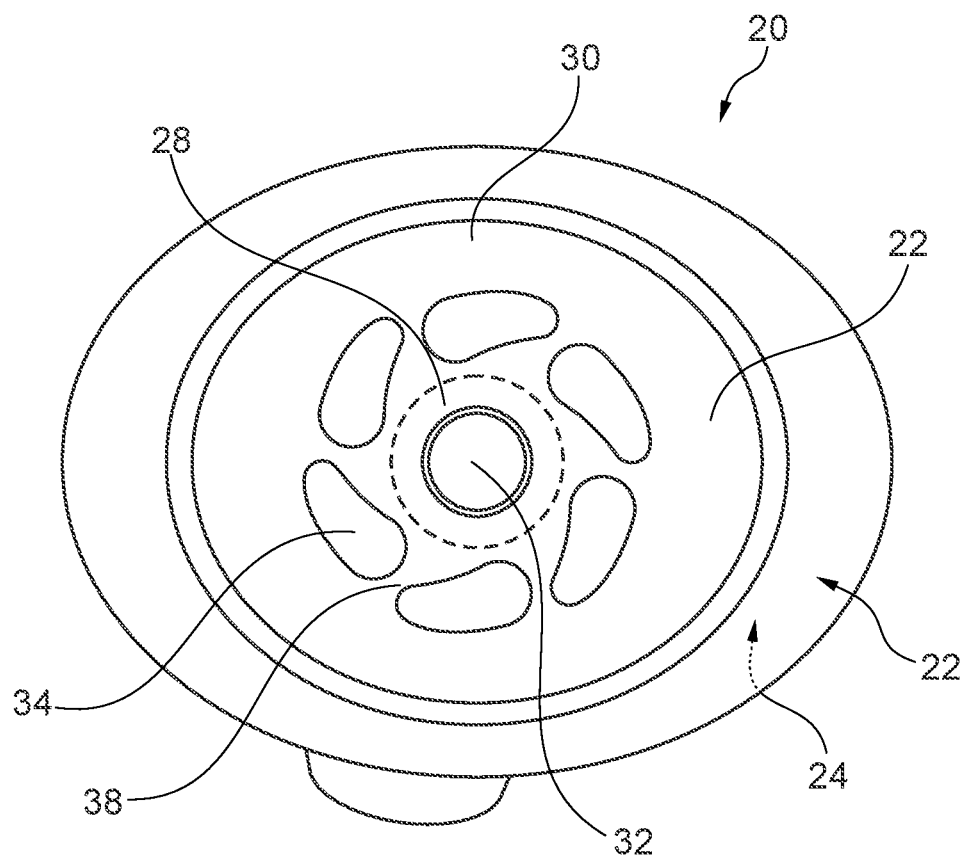
FIG. 1 is a schematic, top view of one embodiment of a body side member of an ostomy appliance.

In the following Detailed Description, reference is made to the accompanying drawings, which form a part hereof, and in which is shown by way of illustration specific embodiments in which the invention may be practiced. In this regard, directional terminology, such as "top", "bottom", "front", "back", "leading", "trailing", etc., is used with reference to the orientation of the Figure(s) being described. Because components of embodiments can be positioned in a number of different orientations, the directional terminology is used for purposes of illustration and is in no way limiting. It is to be understood that other embodiments may be utilized and structural or logical changes may be made without departing from the scope of the present invention. The following detailed description, therefore, is not to be taken in a limiting sense, and the scope of the present invention is defined by the appended claims.

It is to be understood that the features of the various exemplary embodiments described herein may be combined with each other, unless specifically noted otherwise.

Throughout this disclosure, the words "stoma" and "ostomy" are used to denote a surgically created opening bypassing the intestines or urinary tract system of a person. The words are used interchangeably, and no differentiated meaning is intended. The same applies for any words or phrases derived from these, e.g. "stomal", "ostomies" etc. Also, the solid and liquid wastes emanating from the stoma may be referred to as both stomal "output", "waste(s)" and "fluids" interchangeably. A subject having undergone ostomy surgery may be referred to as "ostomist" or "ostomate"—moreover, also as "patient" or "user". However, in some cases "user" may also relate or refer to a health care professional (HCP), such as a surgeon or an ostomy care nurse or others. In those cases, it will either be explicitly stated, or be implicit from the context that the "user" is not the "patient" him- or herself.

In the following, whenever referring to proximal side of a device or part of a device, the referral is to the skin-facing side, when the ostomy appliance is worn by a user. Likewise, whenever referring to the distal side of a device or part of a device, the referral is to the side facing away from the skin, when the ostomy appliance is worn by a user. In other words, the proximal side is the side closest to the user, when the appliance is fitted on a user and the distal side is the opposite side—the side furthest away from the user in use.

The axial direction is defined as the direction of the stoma, when the appliance is worn by a user. Thus, the axial direction is generally perpendicular to the skin or abdominal surface of the user.

The radial direction is defined as transverse to the axial direction that is transversely to the direction of the stoma. In some sentences, the words "inner" and "outer" may be used. These qualifiers should generally be perceived with reference to the radial direction, such that a reference to an "outer" element means that the element is farther away from a centre portion of the ostomy appliance than an element referenced as "inner". In addition, "innermost" should be interpreted as the portion of a component forming a centre of the component and/or being adjacent to the centre of the component. In analogy, "outermost" should be interpreted as a portion of a component forming an outer edge or outer contour of a component and/or being adjacent to that outer edge or outer contour.

In the context of the present disclosure, a "pocket" should be considered a compartment or cavity, i.e. a structure forming, or allowing for, the presence of a volume or space that is surrounded by something and capable of temporarily or permanently holding, enveloping or pouching in something else, such as a mass or volume of a material or substance held in the volume or space.

Moreover, "manipulable material" should be interpreted to include moldable and squeezable materials as well as including permanently deformable and shape-memory materials (i.e. materials capable of recovering to their original shape after a deformation). Also, in alternative implementations, the manipulable material may be non-deformable in itself (i.e. no significant deformation of the dimensions of a mass or volume "per volume unit" of the material is possible). However, it is possible to manipulate the material in the sense of moving it in relation to other components. Additionally, or alternatively, "manipulable" should be interpreted to relate to materials that can be moved and/or manipulated by the hands or fingers of an average person. In one embodiment, the manipulable material is a viscoelastic material.

The use of the phrase "substantially" as a qualifier to certain features or effects in this disclosure is intended to simply mean that any deviations are within tolerances that would normally be expected by the skilled person in the relevant field.

In one aspect, the present disclosure relates to a body side member of an ostomy appliance comprising a proximal surface and a distal surface. At least a portion of the proximal surface comprises an adhesive. The body side member comprises a centre portion. At least the centre portion is prepared for the provision of a stoma receiving opening extending through the body side member. The distal surface of the body side member is configured to comprise one or more pockets, each being configured to hold a manipulable material and to allow the manipulable material to be shifted between at least a first and a second position in the pocket, at least in use of the body side member around a stoma of a user. "At least in use" should be interpreted such that as long as the body side member is not prepared for, or attached to the skin surface of a user, the manipulable material is not intended to be shifted between the first and the second positions.

The proximal surface of the body side member comprises an adhesive. In embodiments, the adhesive comprises a plurality of different adhesive materials. In one embodiment, the different adhesive materials of the adhesive are provided in a side-by-side manner. In one embodiment, the different adhesive materials of the adhesive are provided as a layered structure. In one embodiment, the different adhesive materials of the adhesive are provided primarily side-by-side, but with some overlapping portions of the different adhesive materials. Examples of suitable adhesive materials are given below.

The manipulable material is provided inter alia to provide a better sealing effect between the body side member and that part of the surface of the skin of a user that surrounds the stoma. When the seal or sealing effect is improved, the likelihood of stomal fluids bypassing that seal and cumulating underneath the body side member, i.e. between the user's skin surface and the device, is reduced. However, another important aspect of the disclosure is the finding that any stomal output which does cumulate underneath the body side member, which is almost inevitable to occur during wear of the ostomy appliance, can be rendered unharmful by the shear amount of manipulable material that it engages (and needs to "attack") and/or by incorporation of a neutralizing substance in the manipulable material. The disclosure provides options for rendering the stomal output unharmful even before it can engage with the adhesive on the proximal surface of the body side member. Thereby the often very aggressive bodily substances (e.g. including certain enzymes produced in the body) of the stomal output, are prevented from reaching the polymeric matrix of the adhesive on the proximal surface of the device. This in turn helps to avoid both damage to the skin surface (caused by the aggressive stomal fluids), and disintegration and/or failure of the adhesive. This consequently provides a body side member having improved security against leakage and longer wear time (i.e. the time between substitutions of a used product for a fresh one). A longer product wear time may itself help provide less skin complications, since removal of the adhesive body side member of some appliances currently available from the skin surface has a tendency to strip the skin cells of the epidermis. Thus, by achieving a longer wear time of the product, less product substitutions are required, resulting in fewer occurrences of potential skin cell stripping. Additionally, there is an economic benefit to the user and/or to the health care system/insurance provider, when less substitutions and thus less products are needed.

The present disclosure allows for an improved sealing effect of the body side member to be obtained both "directly", in which case an external surface of a pocket actually engages the surface of the stoma itself to create a seal between the stoma and the external surface of the pocket, and "indirectly", in which case externalization of the manipulable material out of a pocket and into contact with stomal output (and optionally also with the surface of the stoma itself) provides the improved sealing effect. In the latter case, the improved sealing effect is at least partly provided by an increase in the amount of material the aggressive stomal fluids have to break down in order to reach the adhesive on the body side member. The distal surface of the body side member is configured to comprise one or more pockets. This means that the distal surface of the body side member can be provided with the one or more pockets during manufacture such that, when the user receives the body side member, the one or more pockets form(s) is/are present in or on the distal surface. However, it is also envisioned that the one or more pockets may be provided separately from the other elements forming the body side member, such that the user (or the HCP) can provide the one or more pocket(s) to the distal surface of the body side member immediately before application of the product to the skin surface of the user. This additionally allows for individual customization of the body side member. As an example, the user may be able to control both the amount and the optimal location of the one or more pockets on the body side member, i.e. have the option to apply more manipulable material to certain locations where it is mostly needed.

In one embodiment, the one or more pockets are formed as one or more cavities in an adhesive layer provided on both the adhesive side of the proximal surface and on at least a portion of the distal surface of the body side member. The one or more cavities contain the manipulable material. Each cavity may be wholly or only partly filled with the manipulable material. Thereby, it should be understood that configuring the one or more pockets of the distal surface of the body side member to hold the manipulable material also may include forming the pockets without further materials or components than the adhesive of the body side member and the manipulable material. Thus, in embodiments, the one or more pockets are defined as embedded in the adhesive of the body side member, and will be visible as one or more protruding bumps on the distal surface of the body side member. The manipulable material can be "released" by simply pressing on the visible bumps. This can help press or squeeze the proximal surface of the body side member in the locations of the one or more pockets (bumps) towards the skin surface, which may be advantageous in locations where more material is needed to fill a crease or skin fold surrounding the stoma, or in particularly vulnerable locations where the body side member is prone to leakage. Additionally, or alternatively, the user may refrain from providing pressure on the one or more bumps, and instead the manipulable material contained in the one or more cavities will then eventually only be released when the level of breakdown of the adhesive of the body side member reaches the one or more cavities. This may help provide additional control of when and how much manipulable material can and will be released. Moreover, these embodiments may help provide a simpler construction and still achieve the beneficial effects on sealing between the body side member and the skin.

The one or more pocket(s) is/are configured to hold a manipulable material. In one implementation, this means that a pocket is suitable for holding, enveloping or pouching in a mass or volume of the manipulable material or substance. In some embodiments, the one or more pocket(s) form(s) closed, closable or closed-off elements. In other embodiments, the one or more pocket(s) form(s) open or openable elements.

In some embodiments, a total volume or holding space of a pocket is greater than the volume of manipulable material provided in the pocket. In other embodiments, a total volume or holding space of a pocket is substantially filled up with manipulable material such that no, or only an insignificant portion of the volume or space of the pocket is not filled with the manipulable material.

In embodiments, wherein a pocket is formed as a closed-off element, the manipulable material can be configured to be moved around within the confines of the pocket. Thus, in one embodiment, the manipulable material is provided inside the one or more pocket(s) in the first position and in the second position. In other embodiments, in these embodiments the one or more pocket(s) is/are configured such that the manipulable material does not exit from a pocket (including any unintentional exiting).

In embodiments, the improved sealing effect of the body side member can be achieved after applying the body side member to the user's skin surface (adhering the adhesive proximal side to the skin) by providing finger pressure to the exterior of the one or more pocket(s) on the distal surface, to effectively manipulate and thereby move the manipulable material held inside the pocket(s) towards the stoma. The manipulable material can thereby be shifted between at least a first and a second position in (inside) the pocket. In embodiments, a portion of the distal surface of the body side member forming an exterior of the one or more pocket(s) is configured to be brought into engagement or contact with all or a portion of the outer surface, i.e. the mucous membrane, of the stoma, without the manipulable material leaving or exiting the pocket. Thereby, the manipulable material can be shifted between at least a first and a second position in the pocket. In embodiments, the exterior surface of the pocket is configured to be plastically or elastically deformed, such as, but not limited to, using an anisotropic material.

In embodiments, wherein a pocket is formed as an open or openable element or component, the manipulable material is configured to be shifted between at least a first position and a second position within the pocket. However, in some implementations, the pocket(s) comprise(s) one or more openings, such that manipulation of the manipulable material, by providing finger pressure to the exterior of the one or more pocket(s) effectively makes the manipulable material held inside the pocket(s) exit through the one or more openings. Accordingly, the manipulable material can thus be shifted between at least a first and a second position in the pocket. Thus, in one embodiment, the manipulable material is provided inside the one or more pocket(s) in the first position, and at least some of the manipulable material is provided outside the one or more pocket(s) in the second position. As an example: in the case of an open or openable pocket, the manipulable material may in the first position be located in the pocket in a position away from the one or more openings, and then be moved to a second position in (inside) the pocket by finger pressure. Also, in the second position, a first portion or some of the manipulable material may be located inside the pocket and a second portion or some of the manipulable material may be located outside the pocket. In another implementation, the body side member is configured such that substantially all of the manipulable material is located outside of the one or more pocket(s) in the second position.

In one embodiment, the manipulable material is configured to swell in response to absorption of moisture. In embodiments, the manipulable material is configured to undergo a swelling action by absorption of moisture from the stomal output and/or from mucus emanating from the mucous membrane of the stoma. In embodiments, the swelling of the manipulable material helps to create an improved seal between the stoma and the body side member, thereby reducing the probability of leakage caused by stomal fluids attacking the adhesive on the proximal surface of the body side member. In embodiments, the manipulable material includes a moisture absorbing component or substance. In embodiments, the moisture absorbing component has a high absorption capability or potential and in other embodiments, the moisture absorbing component has a small absorption capability. Suitable materials for the moisture absorbing component include, but are not limited to, superabsorbent polymers commonly made from poly-acrylic acid salts.

In one embodiment, the body side member further comprises a reinforcing element. The reinforcing element may particularly, but not exclusively, include a sheet or layer of a polymeric film material, such as polyethylene (PE) or polypropylene (PP). Other film materials having additional characteristics, e.g. higher/lower liquid-, vapor- or gas-impermeability or odour control and others, may additionally and/or alternatively be used. Other reinforcing element options include mesh or mesh-shaped and/or woven materials. In one embodiment, the reinforcing element can be located ("sandwiched") between the adhesive on the proximal surface and the distal surface of the body side member. In one embodiment, the reinforcing element can be embedded (contained completely) in the adhesive of the proximal surface of the body side member. In one embodiment, the reinforcing element includes reinforcing fibres provided on a surface of the body side member. The reinforcing fibres may also be mixed into the adhesive of the proximal surface of the body side member.

One advantageous effect of the reinforcing element is that it helps provide a body side member which is more resistant to forces acting on it. Often a stoma is located on the lower portion of the abdomen of the user (corresponding to the location of the intestines). Thus, some examples of forces acting on the body side member include forces generated by the clothes of the user, such as at the waist lining of a pair of pants or jeans, such forces often further amplified by the presence of a belt. The forces may be both pressure and shear forces, often in combination.

In one embodiment, the distal surface of the body side member comprises a layer of a sheet material. In embodiments, the layer of a sheet material (sheet material layer) is configured to form the distal surface of the body side member. The sheet material layer may particularly, but not exclusively, include a polymeric film material, such as PE or PP. Other film materials having additional characteristics, e.g. higher/lower liquid-, vapor- or gas-impermeability or odour control and others, may additionally and/or alternatively be used. In embodiments, the sheet material layer is dissolvable. In one embodiment, the sheet material layer is dissolvable when subjected to water or a watery liquid, such as aggressive stomal fluids or mucus emanating or secreting from the mucous membrane of the stoma. In one embodiment, the dissolvable material comprises a polyvinyl alcohol (PVA). In one embodiment, the sheet material layer comprises a plurality (i.e. two or more) perforations.

In embodiments, the sheet material layer comprises a woven or a non-woven material. In one embodiment, the sheet material layer is a thermoplastic polymer film. In one embodiments, the sheet material layer comprises an elastic material. In one embodiment, the sheet material layer is suitably capable of transmitting moisture and may e.g. be made from polymers such as polyolefin types e.g. PE, PP or polybutylene, polyamide such as nylon, polyurethane, polyvinyl acetate, polyvinyl chloride, fluorinated polyvinyl compound, polyvinylidene chloride, polyvinyl alcohol, ethylene vinyl acetate, cellulose acetate or other thermoplastic polysaccharides, polyether block amides such as PEBAX® from Arkema, France, block copolymers like styrene-isoprene-styrene block copolymers or ethylene acrylate block copolymers, polyesters such as polyethylene terephthalate (PET) or derivates thereof and any laminates from such polymers. In other embodiments, the sheet material layer comprises a thin foam layer made from e.g. polyurethane, polyethylene or polyvinyl acetate.

In embodiments, a wall of each of the one or more pockets comprises a flexible sheet. In embodiments, the flexible sheet of a pocket wall is made of the same material as the sheet material layer of the body side member. In other embodiments, the flexible sheet is made from a material that is different from the sheet material layer of the body side member. In embodiments, the flexible sheet forming the wall of the one or more pockets comprises a differentiated thickness when viewed over a total extent of the pocket. In one embodiment, a thickness of the wall decreases from a greater thickness at an outer periphery portion of the pocket to be thinner radially closer to the centre portion of the body side member. The differentiated thickness of the wall is believed to be useful in providing a smooth externalization of the manipulable material from the one or more pockets, and also for guiding the manipulable material radially towards the stoma.

In embodiments, a wall of the one or more pockets comprises a thermoformable material. In embodiments, the thermoformable material may be a thermosetting material. In embodiment, one or more walls of a pocket forms a "blisterpack" pocket, such as particularly known from packaging of medicine tablets and/or chewing gum packages. Suitable thermoformable materials include, but are not limited to, rigid PVC materials (polyvinylchlorides materials).

In embodiments, a wall of the one or more pockets is formed by a resilient material. In some implementations, such forming of the wall in a resilient material facilitates the externalization of the manipulable material from the one or more pockets, particularly because the resiliency of the material causes the wall to return to its original/initial shape after an exterior surface of the pocket formed by the wall has been manipulated by finger pressure. Suitable resilient materials for the wall include, but are not limited to, thermoplastic elastomers (TPE's) and/or mixtures thereof. In embodiments, a wall of the one or more pockets is made by injection molding. Alternatively, or additionally, the wall is made in a two-component casting process, advantageously in combination with the provision of a first half of a coupling interface of the ostomy appliance.

In embodiments, any one or both of the flexible sheet forming a wall of the one or more pockets, and the sheet material layer, is/are provided as one or more separate components and is/are configured to be attachable to other components of the body side member. As such, any one or both of these may be "loose" components which is/are provided together with the body side member, but which is/are not initially attached to the body side member (i.e. not attached during the manufacturing process).

In another embodiment, the sheet material layer may be only locally fastened, i.e. the sheet material layer is not attached to the body side member over an entirety of a surface of the sheet material layer. In one embodiment, the sheet material layer is attached to the body side member by hinges or hinge means, including living hinges. In such embodiments, the sheet material layer may be movably attached to the body side member in some locations while not being attached to the body side member in other locations.

In one embodiment, the sheet material layer is formed as an integral component of the structure of the body side member. This means that the sheet material layer is connected to or attached to the body side member during the manufacturing process. In such embodiments, it is thus not a separate component to be subsequently connected to the body side member. The sheet material layer can be connected or attached over an entirety of a surface of the sheet material layer facing the distal surface of the body side member. Alternatively, it can be connected or attached to the surface of the sheet material layer facing the distal surface of the body side member in two or more localized places or points. The attachment or connection to the distal surface of the body side member may be provided by welding, such as heat welding or ultrasound welding, or by adhesion of the components to each other. Adhesion may in such case be provided by the adhesive effect of a distal surface of the adhesive of the body side member or by additional adhesive material being disposed on either the distal surface of the body side member, or on the surface of the sheet material layer facing the distal surface of the body side member. In one embodiment, also at least a portion of the distal surface of the body side member comprises an adhesive. In one embodiment, an adhesive of the proximal surface of the body side member and an adhesive of the distal surface of the body side member are identical adhesives. In one embodiment, one adhesive material forms both the proximal surface and the distal surface of the body side member. Other means or ways of attaching or connecting the components of the body side member to each other may be applied.

In one embodiment, the manipulable material is provided in one or more smaller entities placed inside the one or more pockets at manufacture. "Smaller" should be interpreted to mean that each entity itself does not take up 100% of the volume of each pocket, preferably it takes up no more than 95%, such as no more than 90%, such as no more than 85% of the total volume of a pocket. In one embodiment, each smaller entity takes up approximately 50% of the total volume of a pocket. In one embodiment, each smaller entity takes up approximately 33% of the total volume of a pocket. In one embodiment, each smaller entity takes up approximately 25% of the total volume of a pocket. In one embodiment, each smaller entity takes up approximately 20% of the total volume of a pocket. In one embodiment, each smaller entity takes up approximately 10% of the total volume of a pocket. In one embodiment, each smaller entity takes up approximately 5% of the total volume of a pocket.

In embodiments, the smaller entities may comprise one or more individual balls or spheres of manipulable material provided in the pocket, each of the balls or spheres of manipulable material enclosed by a material which is configured to burst, rip, "crack open" or similar, when the entity is subjected to finger pressure of a user. It is to be understood that finger pressure can be applied to an external surface of a pocket, such that an internal surface of the pocket will contact or "act on" the entity or entities inside the pocket resulting in the ripping or bursting of the one or more entities. In embodiments, wherein a plurality of smaller entities is provided in the one or more pockets, the pocket and entities are configured such that force applied by finger pressure, and acting initially on a first entity inside the pocket, not only serves to rip or burst the first entity, but further is passed on as a translational force to neighbouring entities, such as to also rip or burst open these. In embodiments, the entities can be cylindrical, rod or "sausage"-shaped. The entities may also take other relevant shapes and/or any shape combined by two or more of the shapes mentioned.

In embodiments, the sheet material layer forms the distal surface of the body side member. In embodiments, the proximal surface of the sheet material layer comprises an adhesive forming the proximal surface of the body side member. Pressure sensitive adhesives, particularly those containing hydrocolloids, is a particularly suitable group of adhesives being characterized by having a particulate phase of hydrocolloids dispersed in the adhesive phase or matrix. An adhesive containing hydrocolloids may absorb moisture from the skin avoid occlusion of the skin, while maintaining its adhesive properties to skin. Moreover, and adhesive body containing hydrocolloids may have any thickness and still having the non-occlusive properties. A hydrocolloid adhesive may be processed as a hot melt and is easily moulded into specific shapes.

A typical pressure sensitive adhesive composition comprises a substantially homogeneous mixture of 10-60 weight percent of one or more rubbery elastomeric components, 5-60% of one or more absorbent particles, 0-50% tackifier resin, 0-10% of a plasticiser and 0-60% of a non-polar oily extender, based on the total weight of the composition. The rubbery elastomeric base could be selected from the group consisting of physically cross-linked elastomers (suitably block copolymers containing polystyrene blocks), a chemically cross-linked natural or synthetic rubbery elastomer, or a rubbery homopolymer. A physically cross-linked elastomer selected from block-copolymers of styrene, and one or more butadienes may be a styrene-butadiene-styrene block copolymer, a styrene-isoprene copolymer and is preferably a mixture of styrene-isoprene-styrene and styrene-isoprene block copolymers. A chemically cross-linked rubbery elastomer may be e.g. butyl rubber or natural rubber. A rubbery homopolymer may be a polymer of a lower alkene such as low density polyethylene or propylene, preferably atactic polypropylene or polyisobutylene. A tackifying resin optionally used in accordance with the invention is preferably a hydrogenated tackifier resin and is more preferred selected from a group comprising polymers and copolymers of cyclopentadiene, dicyclopentadiene, alpha-pinene or beta-pinene. When the physically cross-linked elastomer is a styrene-butadiene-styrene block copolymer or a styrene-isoprene-styrene block copolymer, the adhesive suitably comprises 0-10% of a plasticiser (e.g. CITROFOL® BII, Jungbunzlauer, Switzerland). The hydrocolloid particles preferably consist of one or more water-soluble or water swelling hydrocolloid polymers or gums. In other embodiments, the adhesive of the proximal surface of the body side member comprises one or more adhesives of the types disclosed in publications WO2007/082538 and WO2009/006901.

In embodiments, each of the one or more pockets comprises at least one opening providing a passage between an interior and an exterior of each of the one or more pockets. The at least one opening provides a passage for manipulable material to exit through, and/or for liquid or moisture, such as generated by stomal output, to enter through into the pocket. At least in the latter case, a capillary action between the entering moisture, the interior of the pocket and the manipulable material may result in the manipulable material being externalized from the pocket. Moreover, the manipulable material can be configured to swell in response to absorption of moisture which can also cause the manipulable material to externalize and be dispensed from the pocket. Depending, among other factors, on the nature of the manipulable material, in some embodiments moisture absorption and a resulting swelling of the manipulable material initiates the exiting of the manipulable material towards the stoma without any manipulation of the one or more pockets required by the user. In other words, the externalization of the manipulable material from the one or more pockets may start "automatically" as soon the manipulable material begins to take up moisture. It has been found that the rate of the externalization of the manipulable material can be surprisingly high, thereby causing a fast release of the manipulable material. This is helpful in guiding the manipulable material towards the stoma as quickly as possible, thereby providing one way of achieving faster and thus better security against leakage. This is further advantageous because no active participation by the user in externalizing the manipulable material from the one or more pockets is required.

In one embodiment, each of the one or more pocket(s) comprise(s) at least two reservoir portions connected to each other by a transferring portion. Thereby, the manipulable material can be shifted between at least a first and a second position in the pocket, e.g. between a first position in the first reservoir and a second position in the second reservoir. In one embodiment, when the manipulable material is in the second position, it locates in a second reservoir portion of the pocket, into which it has been shifted (moved or relocated by finger pressure/manipulation) from a first reservoir portion of the pocket. In one embodiment, the one or more pockets comprise a single (one and only one) reservoir portion and a transferring portion, the transferring portion connected to the single reservoir portion at a first part of the transferring portion and to the exterior of the pocket at a second part of the transferring portion. In one embodiment, the first and the second parts are provided at opposite ends of the transferring portion. In one embodiment, the manipulable material is located inside the single reservoir of the pocket in the first portion, and at least a portion of the manipulable material is located outside the pocket when it has been shifted to the second position. In embodiments, either of the first and the second reservoir portions can contain a majority of the manipulable material contained in a respective pocket. In embodiments, a majority of the manipulable material is initially contained in one of the reservoir portions, whereas a small or minor portion of manipulable material is at least initially contained in the transferring portion.

In one embodiment, each of the one or more openings of the one or more pockets faces towards the centre portion of the body side member. In one embodiment, at least one opening of the one or more pockets is/are in direct communication with a stoma-receiving opening of the body side member. In such implementations, the at least one opening is particularly suited to allow the manipulable material to be dispensed out of the pocket via the opening into, or near, the stoma-receiving opening. There, the manipulable material can be used to help adapt the body side member to fit to the small folds and creases of the peristomal skin surface and further help create an improved seal between the skin and the body side member. Additionally, the externalization of the manipulable material out of a pocket brings the material into contact with the aggressive stomal fluids and/or with the surface of the stoma itself, also helping to provide the improved sealing effect.

In such embodiments, each opening faces radially inward towards the stoma at least when the body side member is in use on the skin surface of a user. Thereby, any manipulable material exiting a pocket is directed immediately in the direction of any stomal output or moisture emanating from the stoma or the stoma surface. In embodiments, each opening is configured such that it directs manipulable material undergoing swelling in response to moisture absorption, in a radial direction towards an axis being perpendicular to the proximal and distal surfaces of the body side member and extending through the centre portion. Thereby, in use, the opening effectively guides the manipulable material towards the stoma for alleviation of one or more of the problems discussed in this disclosure.

In embodiments, each opening is located at a portion of a pocket that is radially closest to the centre portion of the body side member and axially closest to the distal surface of the body side member.

In another embodiment, each of the one or more openings of the one or more pockets face towards a radially outermost portion of the body side member. This is particularly suitable for helping to provide a distribution of the manipulable material over a larger portion, or even an entirety of the distal surface of the body side member in use, the entirety of the surface being radially inside of either a first half of a coupling interface of the ostomy appliance or a permanent connection between the body side member and a stomal output collecting bag (e.g. radially inside of an annular weld).

In embodiments, the manipulable material comprises a neutralizing substance. The neutralizing substance is very useful for mitigating the damaging effects of the aggressive stomal output. Suitable materials for and characteristics of the neutralizing substance are described in more detail below.

In embodiments, each of the one or more pockets are configured to allow the manipulable material to exit the pocket to be provided externally of the pocket on the distal surface of the body side member, such that manipulable material is available for engagement with stomal output.

In embodiments, the configuration of the one or more pockets allows for manipulable material to be provided externally of the one or more pockets, over substantially an entirety of a portion of the distal surface of the body side member. However, the "entirety" is to be understood as being an entirety of a portion of the distal surface located radially inside of connecting means for connecting the body side member with a stomal output collecting bag.

Thereby, the configuration of the body side member of the disclosure is predominantly directed to achieving protection of the adhesive interface between the skin and the body side member, and to a lesser degree to help filling the small folds and creases of the peristomal skin surface.

Some prior solutions have focussed on addressing these issues at an area of a body side member immediately adjacent to the stoma. Contrary to this, the present disclosure provides different and inventive solutions to these and other problems, because in some approaches, the problems are believed to be mitigated at least partly because of the better options for distributing the manipulable material held in the one or more pockets, such as, but not exclusively, by distributing or "spreading" the manipulable material over a larger or even all of the distal surface and/or proximal surface of the body side member. By having the options of distributing the manipulable material, provided for by the above described embodiments, an area of contact between the aggressive stomal output and a component of the body side member suited for coping with or mitigating the damaging effects of the stomal output (i.e. the manipulable material), is effectively and significantly increased. This is considered particularly advantageous because studies conducted by the inventors have shown that, while it is at least initially the centre portion of the body side member immediately adjacent to the stoma that is engaged ("attacked") by aggressive stomal fluids, in reality a very large portion, or even all of the distal surface of the body side member (radially inside of the collecting bag connecting means), quickly becomes subjected to ("smeared with") the stomal output. According to the invention, the provision of the options of distributing the manipulable material over a large portion of the distal surface of the body side member, being smeared with the aggressive stomal output, means that the manipulable material can engage with the stomal output over a much larger effective "surface area". This is particularly, but not exclusively, advantageous in embodiments wherein the manipulable material comprises a neutralizing substance. The larger surface or area of engagement/interaction between the stomal output and the neutralizing substance means that most of aggressive contents of the stomal output present on the distal surface of the body side member, is/are "neutralized" (rendered not harmful) even before it can enter into contact with the adhesive on the proximal surface of the body side member. Thereby, the adhesive on the proximal surface and adhesive material immediately around the stoma and in the peristomal gap, will not be prone to a fast break-down, in turn providing for an increased wear time as well as a more secure attachment of the ostomy appliance on the skin of the user.

In other embodiments, each of the one or more openings of the one or more pockets is provided in the distal surface of the body side member. In embodiments, the one or more openings is/are provided in an exterior surface of a pocket. The one or more openings can be provided such as to be substantially parallel with the distal surface of the body side member. However, the one or more openings may also be provided at an angle to the distal surface of the body side member. Moreover, the one or more openings may be distributed in a pattern over the exterior surface of the pocket. The pattern may be a symmetrical or a random pattern.

In one embodiment, the one or more pockets is/are provided in a sheet material layer forming the distal surface of the body side member, and the one or more openings of each of the pockets are then provided in the surface of the sheet material layer. In one embodiment, each of the one or more pockets is configured to have an opening over an entire area of a portion of the pocket being parallel to the distal surface of the body side member (i.e. parallel to the radial direction). In other words, the pocket does not have "a surface" that is parallel (extending radially) to the distal surface of the body side member. These implementations can help provide for a prolonged/extended and/or sustained release of the manipulable material, since it can be ensured that the manipulable material is not subjected to immediate attack by the aggressive stomal output. Particularly, the degree of protection of the manipulable material in pockets according to this embodiment, may be varied such as by changing the length of a wall of the pocket between the stoma-receiving opening of the body side member and the opening of the respective pocket being parallel (extending radially) to the distal surface.

In embodiments, each of the one or more openings includes a plurality of openings. In embodiments, the manipulable material is configured to be dispensed from one or more pockets through the one or more openings. Thereby, the manipulable material can be dispensed from a pocket and be directed out of one or more (or even several, such as 5-20 openings) in a particular direction away from the pocket. In embodiments, the one or more openings may additionally be configured to open towards different directions. Thereby, the provision of the one or more openings in the pockets allows for a versatile distribution of the manipulable material. This in turn provides an option for an even distribution of manipulable material out of a pocket and over the distal surface of the body side member. Moreover, this provides a body side member offering many uses while having a relatively simple structure. Additionally, or alternatively, a pocket having a plurality openings may provide an option for differentiating the amount of manipulable material at any locality on the distal surface of the body side member. This is particularly advantageous in that more manipulable material may be guided or directed to a location where it may be more needed than elsewhere on the distal surface of the body side member. This may be, but is not limited to, at a location where the user has an uneven skin surface and thus can benefit from having an increased amount of the manipulable material available to be applied in that particular location (to "fill" any crease or skin fold). Particularly, the manipulable material can be guided both towards the stoma and away from it. This configuration allows for multiple options for addressing the manipulable material's beneficial effects to the right locations, where a leakage problem may be occurring or where the user's experience tells him/her that leakage often occurs. Additionally, or alternatively, one or more of the plurality of openings may face axially away from the distal surface of the body side member, and thus help to direct manipulable material to one or more locations where it is available for an extended period of time compared to when it is immediately subjected to stomal output.

In embodiments, the manipulable material is configured to be dispensed from the one or more pockets. In embodiments, the manipulable material is configured to be actively dispensed. In other embodiments, the manipulable material is configured to be passively dispensed. By 'actively dispensed' is to be understood that in some implementations, in order for the manipulable material to exit a pocket, the pocket should be manipulated by a user's fingers. In other words, 'actively dispensed' should be interpreted to mean that the externalization of manipulable material constitutes an action or step that requires active participation or contribution by the user. In embodiments, an exterior surface of the one or more pockets includes a texture for facilitating easier tactile recognition of where to manipulate the pocket. The texture is further useful in preventing the user's fingers from slipping off the exterior surface of the pocket during such manipulation. By "passively dispensed" is to be understood that in implementations, the manipulable material exits from a pocket by being washed out, dissolved, eroded, broken down etc. by the contents and moisture of the stomal output, i.e. the material is externalized without requiring action by the user.

In embodiments, each of the one or more openings of the one or more pockets is provided in the proximal surface of the body side member. In these implementations, the one or more pockets can be configured such that one or more pockets containing the manipulable material is/are located on, or at, the distal surface of the body side member, whereas the one or more openings of each pocket is/are provided in or on the proximal surface of the body side member. In one embodiment, the opening(s) are provided in the adhesive of the proximal surface of the body side member. In one embodiment, each pocket comprises a first reservoir portion, which holds the manipulable material in the first position, and a transferring portion extending between the first reservoir portion and the opening in, or on, the proximal surface of the body side member, such that, in the second position, the manipulable material can be pressed through the transferring portion and dispensed out of the one or more openings in or on the proximal surface. Thereby the distribution of the manipulable material can be controlled, particularly, but not exclusively, such that additional manipulable material can be directed to a problematic area or location. Such problematic area may be a location in which the user has become aware that leakage has started, or is starting to occur. By providing the opportunity to guide additional manipulable material to the leakage area, the user may buy him- or herself the extra time needed to be able to find a bathroom or other private space, where he/she can change to a new appliance. This is evidently particularly advantageous in helping to support the user's confidence to attend and socialize in the public space. It is well known in the field of ostomy care that the risk of sudden leakage of the product is a stigma to many users, effectively limiting their presence in the public space.

In one embodiment, one or more pockets is/are connected to and in communication with a channel extending from the pocket towards the stoma-receiving opening of the body side member. In one embodiment, the channel extends in a generally radial direction of the body side member from the pocket towards a central longitudinal axis extending through the stoma-receiving opening. Embodiments of the body side member including a channel between a pocket and the stoma-receiving opening provide for the manipulable material to be stored at a distance from the stoma-receiving opening. This in turn allows the user to customize, such as by cutting with a scissors, the stoma-receiving opening to his/her particular stoma size before manipulation of the manipulable material without having to perform the cutting in the manipulable material, which in some implementations can be of relatively soft and sticky nature and thus difficult to cut properly. After the body side member has been applied to the skin surface around the stoma, the manipulable material can subsequently be dispensed from the pocket out into the stoma-receiving opening and adapt to the small folds and creases of the stoma surface, thereby further helping in creating an improved seal between the skin and the body side member.

In one exemplary implementation of such an embodiment, a user initially customizes, such as by cutting, a stoma-receiving opening to an approximate size or circumference of the user's individual stoma. By cutting the stoma-receiving opening, which may in some cases be located in the first zone of the sheet material layer, the user can simultaneously cut or otherwise open one or more of the individual pockets to allow passage between manipulable material inside the pocket and the exterior of the pocket. Next, the user can remove any protective liner(s) provided on the body side member, such as on the adhesive of the proximal surface of the body side member and apply the body side member to the skin surface around the stoma. The user can then apply finger pressure to each of the one or more individual pockets to dispense the manipulable material out of the one or more pockets.

In embodiments, the one or more pockets is/are configured to be attachable to the distal surface of the body side member. Thereby, each pocket forms a component that is initially separate from the body side member and is attached as such to the distal surface or to the proximal surface or both of the body side member. In some implementations, such separate structure of the one or more pockets facilitates the manufacture of the body side member in that the manipulable material and the pocket can be produced and prepared in a process independent of producing the other components of the body side member and/or of the stoma appliance. This is advantageous because relevant process parameters for handling the manipulable material (e.g. temperature and pressure) and the adhesive of the proximal surface of the body side member can be significantly different from each other.

From the above, it is understood that in conceiving the invention of the present disclosure, the inventors realized that the manipulable material does not per se have to be provided close to, or in direct contact with the stoma's surface, or on the peristomal skin surface, in order for the manipulable material to provide its beneficial effect on the sealing between the skin surface and the body side member. Indeed, it was realized that the effect is achievable to a significant extent by releasing manipulable material on the distal surface of the body side member, i.e. on the surface of the body side member facing away from the skin of the user, when the body side member is used.

Other helpful effects are envisioned by the body side member according to the disclosure, some of which effects are believed to be at least partly controllable by the applied number of pockets and by the composition of the manipulable material. In embodiments, the pocket(s) comprise(s) more than one kind of manipulable material. In embodiments, different pockets contain different manipulable materials. Thereby, it is believed that more than one helpful effect can be achieved by the body side member. Even further, as an example, in embodiments wherein more than one kind of manipulable material is provided in one or more pockets of the body side member, the helpful effect(s) presented by one manipulable material may be amplified by the presence of another kind of manipulable material to provide even better results in terms of reduction or elimination of leakage incidents.

In embodiments, the distal surface of the body side member comprises a first half of a coupling interface for coupling the body side member to a stomal output collecting bag. In one embodiment, the coupling half is a flange adapted to provide a surface for attaching another coupling half in the form of an adhesive flange provided on a stomal output collecting bag. In embodiments, the first half of the coupling interface is configured as a flexible, planar annular flange optionally comprising an adhesive. The first coupling half is adapted to couple with a second coupling half provided around an inlet opening of a stomal output collecting bag by means of an adhesive. The adhesive coupling may provide a releasable or a permanent adhesive coupling engagement between the components.

In embodiments, the coupling half is an annular ring comprising an upstanding flange protruding from the distal surface perpendicular thereto for attaching another coupling half in the form of a coupling ring provided on a stomal output collecting bag. In one embodiment, a first coupling half is attached to the distal surface of the body side member. In embodiments, the first coupling half is attached to the distal surface by an adhesive or by welding, but other ways of attaching are acceptable. In embodiments, a first coupling half is attached to the distal surface of the body side member at a location radially closer to the stoma-receiving opening than where the one or more pockets is/are located. In embodiments, a channel extends from the one or more pockets under (below) the location of attachment of a first coupling half to the distal surface of the body side member. In embodiments, one or more pockets is/are provided distally of the distal surface of the body side member and proximal to a first half of a coupling interface for connection of the body side member to a stomal output collecting bag. In embodiments, the first half of the coupling interface is attached to a distal-most portion of one or more pockets.

In embodiments, the upstanding flange of the annular ring of the first coupling half comprises one or more hollow sections. The one or more hollow sections form one or more compartments each configured to contain a mass or volume of manipulable material. In embodiments, a radially innermost wall of the upstanding flange comprises at least one opening providing a communication passage between the manipulable material in the one or more hollow sections or compartments, and the portion of the distal surface of the body side member radially inside of the annular ring of the first coupling half.

In embodiments, the first half of the coupling interface comprises an inner annular ring and an outer annular ring, the outer annular ring further comprising alternating hollow and solid sections in an internal portion of the outer annular ring, which is configured to receive the inner annular ring therein. The inner annular ring is attached to the distal surface of the body side member and is provided with one or more loading sections configuring to forming one or more pockets, which are adapted to hold a mass or volume of manipulable material. The hollow sections of the outer annular ring are configured to initially mate with the loading sections or pockets of the inner annular ring. In embodiments, the inner annular ring and the outer annular ring are configured to be rotatable in relation to one another. A radially innermost wall (in relation to the centre portion of the body side member) of the outer annular ring comprises at least one opening coinciding with a hollow section of the outer annular ring. When the outer annular ring and the inner annular ring are rotated in relation to each other, the solid sections of the outer annular ring move into the manipulable material contained in the loading section or pocket of the inner annular ring, and thereby acts to dispense manipulable material out of an opening, onto the portion of the distal surface of the body side member radially inside of the outer annular ring.

These embodiments may be particularly advantageous because any pressure applied to the first and second coupling halves, and in particular pressure applied when connecting a stomal output collecting bag to the body side member, may result in pressure forces being transferred by the first coupling half on the one or more pockets to the manipulable material inside each of the pockets, thereby causing manipulable material to be dispensed from the pocket or loading section. In this manner, both the coupling procedure and the dispensing of the manipulable material can be achieved in only single action by the user.

In embodiments, the distal surface of the body side member comprises one single pocket. One single pocket should be interpreted to mean one and only one pocket. Among other advantages, this provides for a body side member to be produced involving less complicated production steps.

In embodiments, the single pocket is configured to extend annularly around the centre portion of the body side member. Among other advantages, these embodiments are particularly suitable for a relatively simple production process.

In embodiments, the first coupling half is configured as an annular ring including an upstanding flange extending axially away from the distal surface of body side member. In one embodiment, the upstanding flange is configured to be perpendicular to the distal surface of the body side member. In one embodiment, the first half of the coupling interface is attached to a distal-most portion of the single pocket. In one embodiment, the single pocket has an outer perimeter that defines a first, outer diameter D1 being greater than a second, maximum outer diameter D2 of the annular ring forming the first half of the coupling interface.

In embodiments, one or more openings of a pocket is/are located immediately above ("over") or adjacent the distal surface of the body side member. In embodiments, the single pocket includes a reservoir portion containing a major portion of the manipulable material. In embodiments, the single pocket including the reservoir portion is defined by a wall of the pocket extending generally in an "S"-shape configuration including a proximal flange, a connecting flange and a distal flange. In embodiments, the reservoir portion is connected to an opening via a canal. In embodiments, the manipulable material is configured to be in fluid communication between the reservoir portion and the opening via the canal. Thereby, the size of the reservoir portion and/or the externalization characteristics (such as, but not limited to, speed of exiting manipulable material, finger pressure needed, ejection direction etc.) can be configured according to needs.

In embodiments, the one single pocket comprises a plurality of openings or gates. In embodiments, the gates need not be of the identical magnitudes/sizes such as to provide a further option for differentiating the distribution of the manipulable material on the body side member.

In embodiments, a protrusion extends distally from the distal flange. In embodiments, the protrusion provides at least a radial abutment of the pocket against which an annular ring of the first half of the coupling interface can abut.

In embodiments, only a minor surface portion of the manipulable material is exposed at each opening. Thus, a relatively small amount of manipulable material is not confined by the wall/flanges of the single pocket present at the gap of the opening. This is advantageous in that it allows for controlling where and how quickly moisture and exudates from the stomal output can "attack" the manipulable material. In other words, the structure of the single pocket protects the manipulable material from being exposed to stomal output from more than one side. These embodiments are further advantageous in that the manipulable material will not be immediately visible to the user, thereby providing a visually simpler impression of the ostomy appliance. Moreover, because the manipulable material is generally protected in the single pocket, the distal surface of the body side member can be cleaned (wiping off stomal output and already eroded/used manipulable material) during an exchange of the stomal output collecting bag without inadvertently also removing still viable manipulable material.

In one embodiment, the body side member comprises a first half of a coupling interface for connection of the body side member to a stomal output collecting bag, wherein the one or more pockets is/are adapted to be attachable to the first half of the coupling interface. Thereby, the one or more pockets may be attached to the first half of the coupling interface during manufacture of the body side member, or the one or more pockets may be attached to the first half of the coupling interface by a separate action of the user, i.e. the one or more pockets are attached to the coupling part just before use, i.e. just prior to the body side member being connected to the stomal output collecting bag. In embodiments, the one or more pockets may be adapted to be attachable to the second half of the coupling interface, i.e. the one or more pockets may be attached to the coupling part of the stomal output collecting bag just prior to the body side member being connected to the stomal output collecting bag.

In one embodiment, the first half of the coupling interface comprises an upstanding flange extending axially away from the distal surface of the body side member. In one embodiment, the upstanding flange is configured to be perpendicular to the distal surface of the body side member. In one embodiment, the upstanding flange forms an annular ring.

In one embodiment, the one or more pockets is/are configured to be attached to the first half of the coupling interface by a snapping or clipping mechanism. Each of the one or more pockets can be provided as one or more individual components. In embodiments, a pocket component comprises a reservoir portion holding the manipulable material and further comprises one or more attachment flanges. In embodiments, one or more attachment flanges protrude from an exterior surface of the reservoir portion. The one or more attachment flanges are adapted to be attached to the first half of the coupling interface such as to snap or clip into attachment with the first coupling half. From its position attached to the first half of the coupling interface, each of the pockets are available for externalizing the manipulable material held inside. In embodiments, the reservoir portion is formed from a material that is adapted to burst or break, when subjected to finger pressure, as discussed above in relation to other embodiments.

In embodiments, the one or more pockets are adapted to be attached to a radially innermost portion of the first half of the coupling interface. In other embodiments, the one or more pockets are configured to allow the reservoir portion to be located on the body side member radially outside of the coupling interface, in use of the body side member. In such embodiments, the one or more pockets may further comprise a transferring portion, channel or canal which is adapted to bypass the coupling interface to allow the user to dispense manipulable material onto the distal or proximal surface of the body side member. Particularly, but not exclusively, this may be advantageous to allow for manipulable material to be dispensed after some time has passed since the user exchanged the appliance. This may help increase the total wear time of the body side member, thereby resulting in fewer product changes and less skin irritation.

In embodiments, the one or more pockets is/are provided along an inner periphery of an annular insert, the annular insert configured to engage with an annular ring of the first half of the coupling interface by snapping or clipping onto the annular ring, such that the annular insert is located radially closer to the central portion of the body side member than the annular ring. In other words, the annular insert is located on and along an inner peripheral portion of the annular ring of the first half of the coupling interface. This provides a simple and intuitive option for the user to attach the annular insert with the one or more pockets containing the manipulable material to the body side member. However, the annular insert may instead be adapted to be attached to the second half of the coupling interface provided on the stomal output collecting bag, while providing the same or similar beneficial effects. An advantage of the embodiments of the body side member disclosed herein, is that a user adapting stoma receiving opening of the ostomy appliance before application to the skin, such as by cutting with a pair of stoma scissors, does not have to be concerned with cutting away or removing viable manipulable material. Applying the one or more pockets in a body side member ensures that the manipulable material from manufacture is provided sufficiently remote from the centre portion prepared for the individual user customization of the stoma receiving opening.

The Neutralizing Substance

By neutralizing substance is herein meant a substance capable of neutralizing or at least minimizing the level of skin- or adhesive-aggressiveness of the output. In embodiments, the neutralizer comprises a clay, such as organophilic clay, for example bentonite or synthetic clay such as laponite. In embodiments, the neutralizing substance may be potato-derived inhibitors or protease inhibitors. Examples of potato-derived inhibitors such as potato protein is disclosed in EP 1 736 136.

In embodiments, the manipulable material is in the form of a matrix composition with a neutralizing substance incorporated. The neutralizing substance may be dissolved in the matrix composition or it may be dispersed as particles in the matrix. In embodiments, the matrix may be in the form of coated neutralizing substance particles.

In embodiments, the matrix is designed to release neutralizing substance to the environment when the matrix is exposed to certain conditions. Such conditions may for example be in the presence of output from the stoma or in the presence of moisture as such.

In embodiments, the matrix is in the form of a gel, foam, film layer or paper or a coating.

In embodiments, a suitable example of a matrix composition could be an adhesive comprising 50% w/w polyisobutylene (PIB) and 25% w/w CMC and 25% w/w pectin.

In embodiments, a matrix composition in the form of a water-soluble film could be a PVOH based thermoplastic film, such as a Monosol® 7031 film from kurakay WS Film Division™, Portage, Ind., United States.

In embodiments, the matrix is soluble in water or a component of the output. It may be slowly soluble, by slowly is herein meant that the matrix layer will not be washed away instantly, but will slowly dissolve during wear time of the wafer.

In embodiments, the matrix can absorb moisture and turn into a gel like material when wetted. The gel may be delivered in dry form but swell into a gel when brought into contact with moisture. The gel may be slowly soluble in water or in a component of the output or it may be insoluble but able to release the neutralizing substance when exposed to the output or moisture.

In embodiments, the matrix comprises polysaccharides and/or hydrocolloids. The polysaccharides or hydrocolloids may dissolve or hydrate when exposed to output, thereby releasing neutralizing substance.

In embodiments, the matrix comprises protein. In embodiments, the matrix comprises gelatine.

In embodiments, the matrix is a material capable of forming a gel when wetted. Examples of suitable materials for the matrix composition may be polyethylene glycol (PEG), polyvinyl alcohol (PVA), polyvinyl pyrrolidone (PVP), ethylene vinyl acetate (EVA) based matrix and hydrocolloids such as CMC or gelatine. In embodiments, the matrix is substantially non-adhesive. By non-adhesive is meant that it is not adhesive, though it may under certain circumstances become slightly sticky.

In another aspect, the disclosure relates to an ostomy appliance including a body side member as described herein and a stomal output collecting bag configured to be attached to the distal surface of the body side member.

In one embodiment, the ostomy appliance is a one-piece ostomy appliance, i.e. without a coupling interface between the body side member and the stomal output collecting bag. In another embodiment, the ostomy appliance is a two-piece appliance including a coupling interface for connecting a stomal output collecting bag to the body side member by connecting or coupling first and second coupling halves to each other.

In one embodiment, the stomal output collecting bag comprises a second half of a coupling interface that is configured to couple with a first half of the coupling interface on the body side member to attach the stomal collecting bag to the body side member.

In one embodiment, at least the distal surface of the body side member is defined by a first zone and a second zone surrounding the first zone, the first zone being radially inside of an annular connection between a first half of a coupling interface and the body side member, and the second zone being radially outside of the annular connection between the first half of the coupling interface and the body side member.

In one embodiment, each of the one or more pockets are located in the second zone of the distal surface of the body side member. In embodiment, one or more canals or openings are provided and create a passage between each of the pockets and the distal surface of the body side member for externalizing the manipulable material and delivering it onto preferred locations on the distal surface 22.

In embodiments, the manipulable material comprises an adhesive. In other embodiments, the manipulable material comprises a powder. In other embodiments, the manipulable material comprises a liquid. In other embodiments, the manipulable material comprises a gel. In other embodiments, the manipulable material comprises a plurality of pellets. In yet other embodiments, the manipulable material comprises a combination of any one or more of an adhesive, a powder, a liquid, a gel and/or a plurality of pellets. These options each provides one or more different advantages including, but not limited to, manipulability, shelf life, suitability for different kinds of stomal output (colostomy output tends to be much more solid than ileo- and urostomy output), processing characteristics and others. By selectively applying these options, individually or in combination, to meet particular requirements of a target ostomy group, the suitability of the appliance and the improvement in sealing effect reducing or eliminating the risk of leakage, can be significantly enhanced.

Particularly, in embodiments wherein the manipulable material comprises an adhesive, suitable materials include adhesives, such as, but not limited to, adhesive pastes. Suitable materials for a paste-type adhesive comprise adhesives of the types disclosed in WO2010/069334. Other types of adhesive pastes are also acceptable.

In embodiments, the shifting between the first and the second positions of the manipulable material inside the pocket does not cause externalization of manipulable material from the pocket.

DETAILED DESCRIPTION OF THE DRAWINGS

Figure 2:
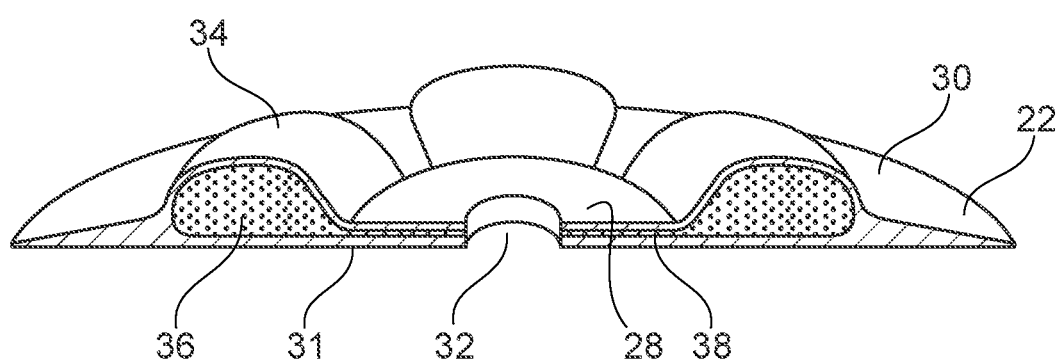
FIG. 2 is a schematic cross-sectional view of one embodiment showing a body side member comprising manipulable material.

FIG. 1 is a top view of one embodiment of a body side member 20 of an ostomy appliance according to the present disclosure. The body side member 20 includes a distal surface 22 ("overside" in FIG. 1) and a proximal surface 24 ("underside" in FIG. 1). The distal surface 22 comprises a first zone 28 and a second zone 30 surrounding the first zone 28. At least a portion of the proximal surface 24 of the body side member 20 comprises an adhesive 31 (FIG. 2). FIG. 1 shows a centre portion 28 of the body side member 20 which has been provided with a stoma receiving opening 32. The stoma receiving opening 32 may be provided during manufacture of the body side member 20, or it may be provided by the user in preparing the body side member 20 for attachment to the skin surface around his or her stoma.

Moreover, FIG. 1 shows how the distal surface 22 of the body side member 20 comprises one or more pockets 34 (FIG. 1 illustrates six pockets). Each individual pocket 34 may take any appropriate shape, such as having the somewhat rounded or bean-shaped contour shown in FIG. 1, or a more circular, cylinder, linear or square contour or any combination of those.

Each of the one or more pockets 34 are configured to hold a manipulable material 36 (FIG. 2). Thus, each pocket 34 is suitable for holding, enveloping or pouching in a mass or volume of the manipulable material 36. Each of the one or more pockets 34 are configured to allow the manipulable material 36 to be shifted between at least a first position and a second position in the pocket 34. The manipulable material is shiftable between the first and the second position in the pocket at least in use of the body side member 20. In FIG. 1 and FIG. 2, the one or more pockets 34 each form a closed, closable or closed-off element or component.

FIG. 2 is a schematic cross-sectional view of one embodiment of the body side member 20 comprising closed pockets 34 containing a manipulable material, in this case a manipulable material 36 being moldable. By applying finger pressure to an outer or exterior surface of each of the closed pockets 34, the manipulable material 36 can be shifted between a first position and a second position in a respective pocket 34. This principle is further illustrated in FIGS. 3 and 4.

Figure 3:
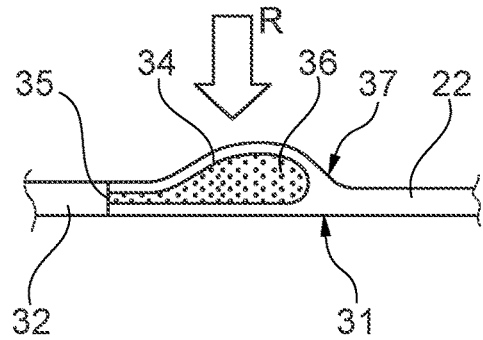
FIG. 3 is a schematic cross-sectional detail view of one embodiment illustrating a portion of a body side member.
Figure 4:
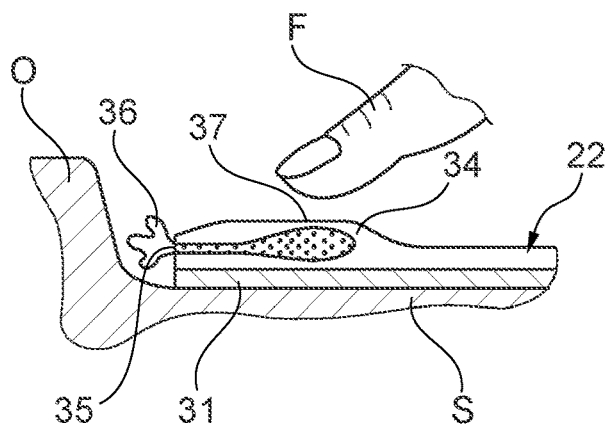
FIG. 4 is a schematic cross-sectional detail view of one embodiment illustrating a portion of a body side member.

FIGS. 3 and 4 are schematic cross-sectional views illustrating a portion of the body side member 20 in place on the skin surface S around a stoma O of a user and particularly showing one embodiment of an open or openable pocket 34 containing a mass or volume of manipulable material 36. The body side member 20 is adhered to a peristomal area of the skin surface S by the adhesive 31. FIG. 3 illustrates the manipulable material 36 being in the first position in the pocket 34. As indicated by arrow R in FIG. 3, the manipulable material 36 in the pocket 34 can be subjected to finger pressure from a user. This causes the manipulable material 36 to be shifted to the second position in the pocket 34 as illustrated in FIG. 4 where finger F of a user is shown which provides pressure to the pocket 34 to dispense in an active manner the manipulable material 36 from the pocket 34.

The manipulation of the manipulable material by finger pressure on an exterior surface 37 of the pocket 34 effectively makes the manipulable material 36 held inside the pocket 34 exit, or be dispensed from the pocket 34 through one or more openings 35 (in FIGS. 3 and 4 only one opening 35 is shown). Accordingly, the manipulable material 36 can thus be shifted between at least a first and a second position in the pocket 34, in which case the manipulable material 36 is provided inside the pocket 34 in the first position, and at least some of the manipulable material 36 is provided outside the pocket 34 in the second position. This is illustrated in FIG. 4. FIG. 4 further illustrates the pocket 34 having a reduced axial protrusion after some dispensing of manipulable material 36.

In FIGS. 3 and 4, only one opening 35 is shown. Opening 35 is provided in a wall of the pocket 34 such that the opening 35 faces towards the centre portion 28 (FIG. 1) of the body side member 20.

Figure 5:
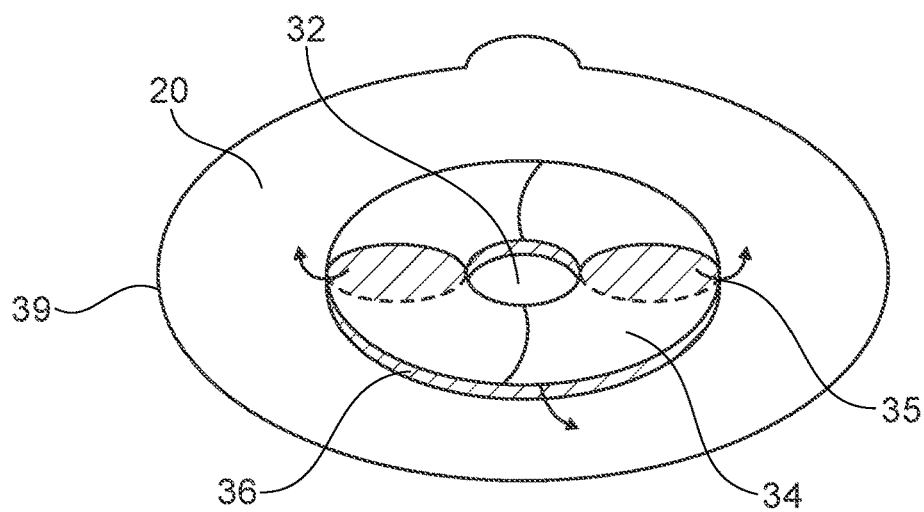
FIG. 5 is a schematic cross-sectional view of one embodiment showing a body side member comprising manipulable material.

FIG. 5 is a schematic cross-sectional view of one embodiment of an open pocket 34 of a body side member 20 containing manipulable material 36, which face towards a radially outermost portion 39 of the body side member. When finger pressure is exercised on the outer surface of the pocket 34, the manipulable material 36 exits from the pocket 34 via opening 35. The manipulable material 36 is thereby directed or guided from the pocket 34 and out onto the distal surface 22 of the body side member 20. This will help the user to distribute the manipulable material 36 over a larger, or even an entirety of the distal surface 22. Additionally, visible is a cross-sectional contour of a first half 40 of a coupling interface for connecting the body side member 20 to a stomal output collecting bag (not shown) provided on the distal surface 22.

Figure 6:
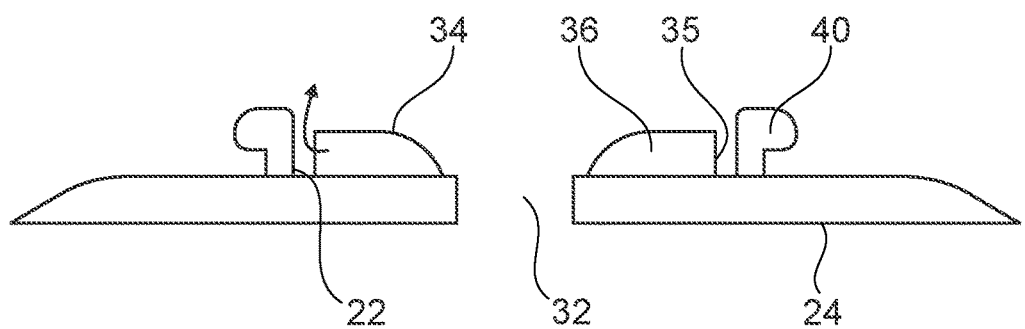
FIG. 6 is a schematic perspective view of one embodiment of a body side member.

FIG. 6 is a schematic, perspective view of one embodiment wherein a pocket 34 is illustrated as a single annular pocket 34 having a single annular opening 35. The manipulable material 36 is dispensable from one or more openings 35, which face towards a radially outermost portion 39 of the body side member 20.

Figure 7:
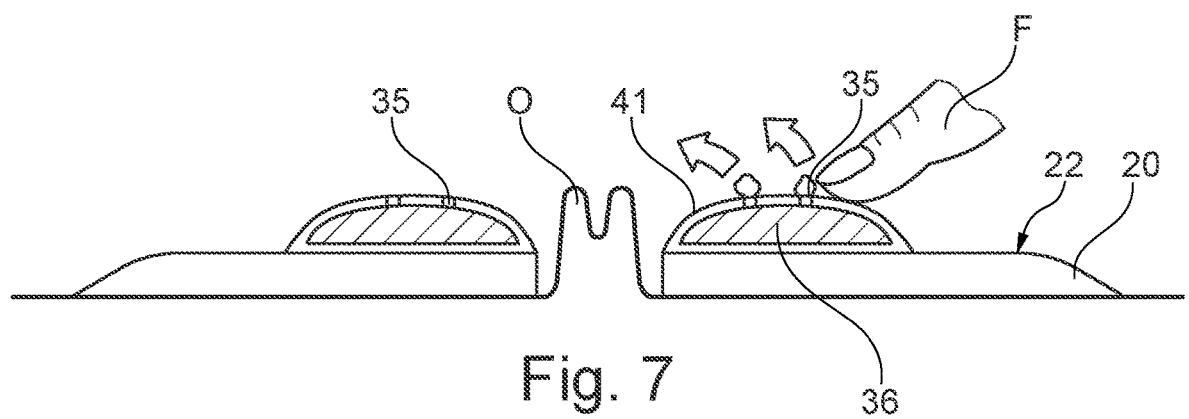
FIG. 7 is a schematic, cross-sectional view illustrating one embodiment of a body side member.

FIG. 7 is a schematic cross-sectional view illustrating one embodiment comprising an open pocket 34 having at least two openings 35 provided in a portion 41 of the pocket 34 in the distal surface 22 of the body side member 20. When finger pressure is exercised on the outer surface of the pocket 34, the manipulable material 36 at least initially exits from the pocket 34 via openings 35 in a direction axially away from the distal surface 22. The manipulable material 36 can be directed or guided out of the openings 35 of the pocket 34 and onto both the distal surface 22 of the body side member 20, and into contact with the surface of the stoma O. This can help the user to distribute the manipulable material 36 over a different and/or a larger portion, or even over an entirety of the distal surface 22, while it is also possible to provide an improved sealing effect between the stoma O and the body side member 20 by simultaneously directing manipulable material 36 towards the surface of the stoma O.

Figure 8:
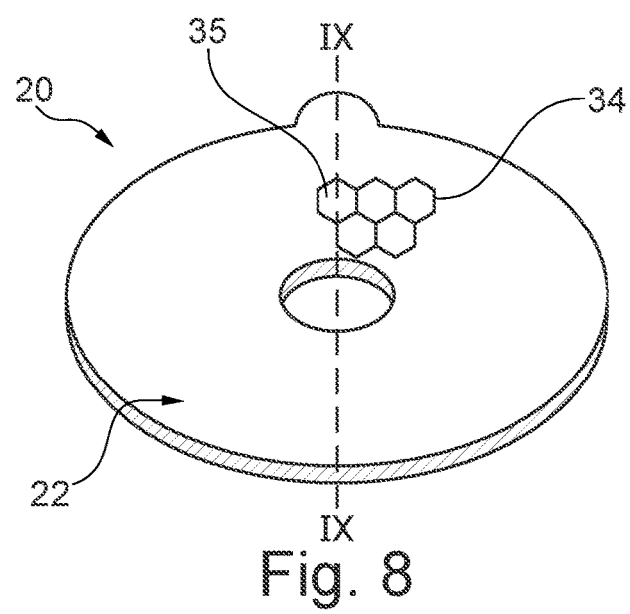
FIG. 8 is a schematic top view showing a distal surface with openings to one or more pockets of one embodiment of a body side member.

FIG. 8 is a schematic perspective view of one embodiment of a body side member 20, wherein one or more openings 35 of one or more pockets 34 containing manipulable material 36 are provided in the distal surface 22 of the body side member 20. In embodiments, each opening 35 and/or each pocket 34 has a hexagonal shape. In embodiments, each pocket 34 is formed as an individual compartment containing the manipulable material 36.

Figure 9:
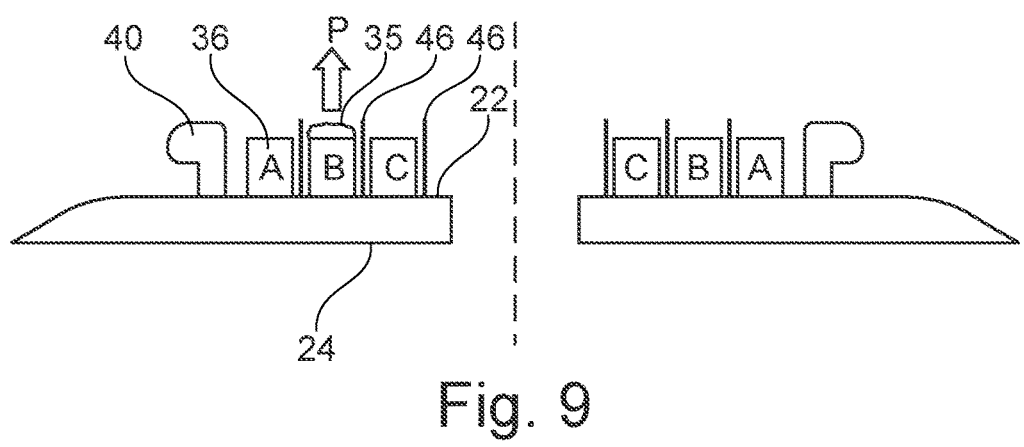
FIG. 9 is a schematic, cross-sectional view of one embodiment of a body side member.

FIG. 9 is a schematic cross-sectional view taken along line IX-IX of FIG. 8, and illustrating how the manipulable material 36 is held in a plurality of pockets 34 forming different compartments 44 separated by walls 46. Each of the pockets 34 are open with an opening 35 which faces in the distal direction. As such, the manipulable material 36 may thereby be released or dispensed in a distal direction, i.e. away from the skin surface of a user when the body side member 20 is in use, as indicated by arrow P in FIG. 9. This allows the dispensed manipulable material to "spread" over a larger area of the distal surface 22 of the body side member 20.

Figure 10:
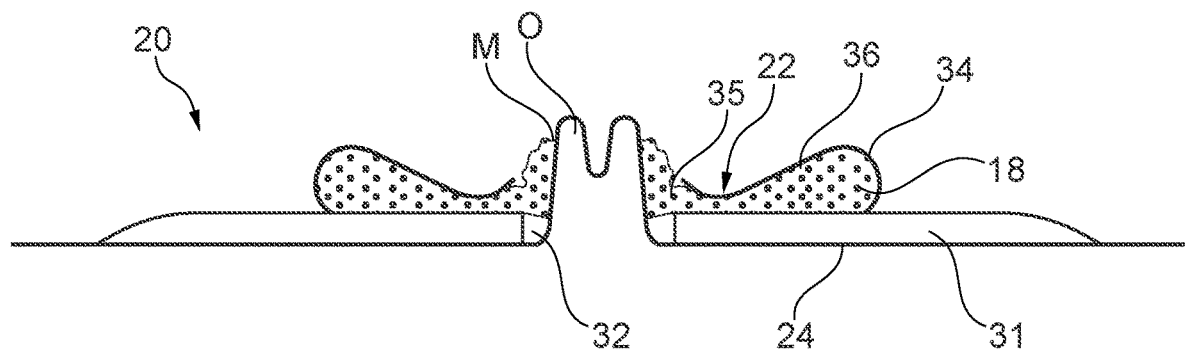
FIG. 10 is a schematic cross-sectional view of one embodiment of a body side member.

FIG. 10 is a schematic cross-sectional view of one embodiment of a body side member 20 comprising an open pocket 34 containing a mass of manipulable material 36. The manipulable material 36 of FIG. 10 is configured to comprise a moisture absorbing material. An opening 35 faces towards the centre portion of the body side member and thus towards the stoma O. This allows both for manipulable material 36 to be dispensed and guided towards the stoma O and for allowing the moisture absorbing material of the manipulable material 36 in the pocket to absorb moisture M from the mucous membrane of the stoma. In this way, the open pocket 34 of FIG. 10 can be considered to comprise or form a moisture or mucus trap 48, which takes up excessive amounts of these fluids. Depending on the amount of and content of moisture absorbing material in the total manipulable material 36, the moisture absorption rate can be varied. Since the moisture trap 48 is configured to absorb the excessive fluids before they reach the proximal surface 24 comprising the adhesive 31 of the body side member 20, the wear time of the body side member can be effectively extended.

Figure 11:
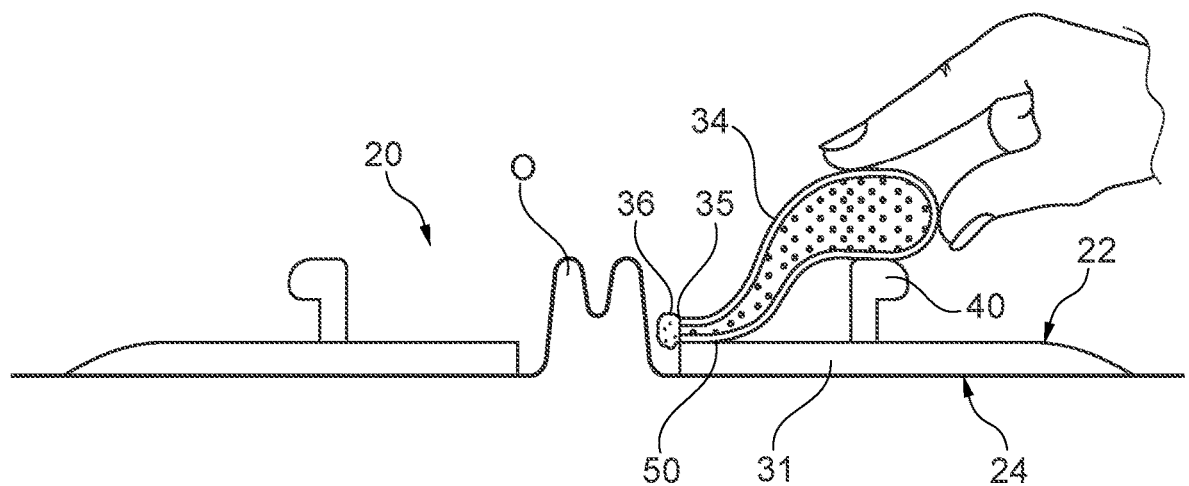
FIG. 11 is a schematic, cross-sectional view of one embodiment of a body side member.

FIG. 11 is a schematic cross-sectional view of one embodiment of a body side member 20 comprising an open pocket 34 containing a mass of manipulable material 36. The open pocket 34 of FIG. 11 is configured to be attachable to the distal surface 22 of the body side member 20. Thereby, the pocket 34 forms a component that is initially separate from the body side member 20 and which is configured to be subsequently attached to the distal surface 22 of the body side member 20. The pocket 34 has an opening 35 shown in FIG. 11 to face towards the stoma O. FIG. 11 further illustrates how finger pressure externalizes and dispenses manipulable material 36 from the pocket 34 through opening 35. The pocket 34 of FIG. 11 is shown to be attached to the distal surface 22 in an attachment zone 50 at an innermost portion of the distal surface 22 of the body side member 20. The attachment can be provided by an adhesive bond of a mechanical fastening, such as, but not limited to, hook- and loop-type fastenings. The configuration of the embodiment of FIG. 11 allows the manipulable material 36 to absorb moisture M from the mucous membrane of the stoma and is configured to absorb excessive fluids from the stoma O before these reach the proximal surface 24 comprising the adhesive 31 of the body side member 20, thus providing for the wear time of the body side member to be effectively extended. The user may also choose to locate the pocket 34 at other locations on the distal surface 22 of the body side member 20. To this end, the distal surface 22 can be sticky itself or comprise a top layer of mechanical fastening, such as, but not limited to, hook- and loop-type fastening.

Figure 12:
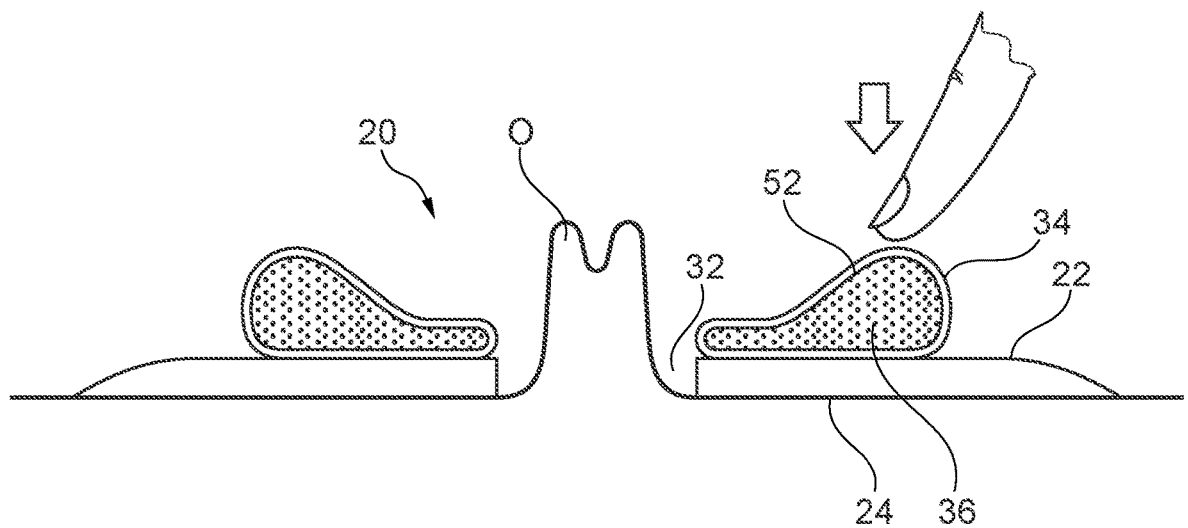
FIG. 12 is a schematic, cross-sectional view of one embodiment of a body side member.
Figure 13:
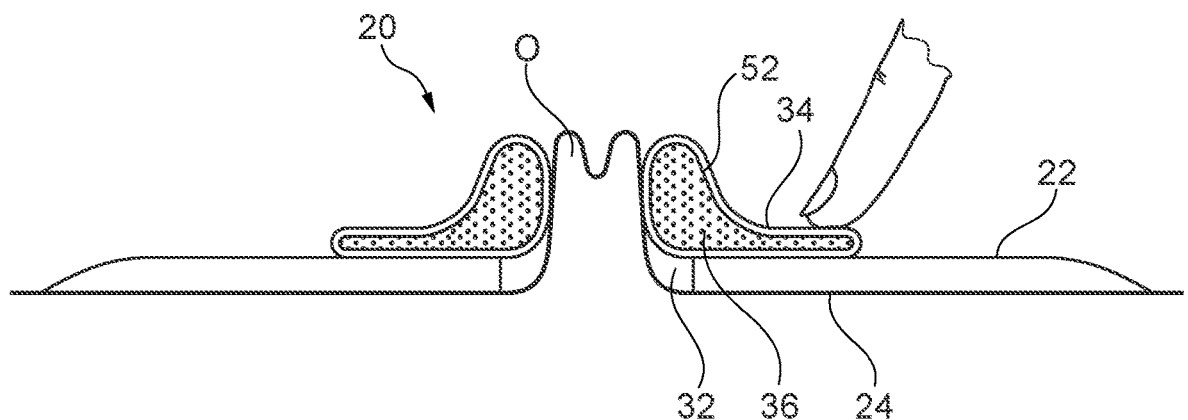
FIG. 13 is a schematic, cross-sectional view of one embodiment of a body side member.

FIGS. 12 and 13 are schematic cross-sectional views of one embodiment of a body side member 20 comprising a closed pocket 34 containing a mass of manipulable material 36. FIG. 12 shows the closed pocket 34 containing the manipulable material 36 in a first position in the pocket in use of the body side member 20 around a stoma O of a user. FIG. 13 shows the closed pocket 34 containing the manipulable material 36 in a second position in the pocket in use of the body side member 20 around a stoma O of a user. In the first position in FIG. 12, at least a majority of the manipulable material 36 is held in a first reservoir portion 52 of the pocket 34. In the second position in FIG. 13, a majority of the manipulable material 36 has been shifted to a second reservoir portion 54 of the pocket 34 by applying finger pressure on an exterior surface of the pocket 34. In the second position shown in FIG. 13, an exterior surface 56 at the second reservoir portion 54 of the pocket 34 engages the mucous membrane of the stoma O. This allows for an improved sealing effect of the body side member 20 obtained "directly", as the exterior surface 56 of the pocket 34 actually engages the surface of the stoma O itself and creates a seal between the stoma and the external surface 56 of the pocket 34, thereby preventing fluids from the stoma O to reach the proximal surface 24 of the body side member 20. This in turn allows for greater security against leakage and for extending the wear time of the body side member 20.

Figure 14:
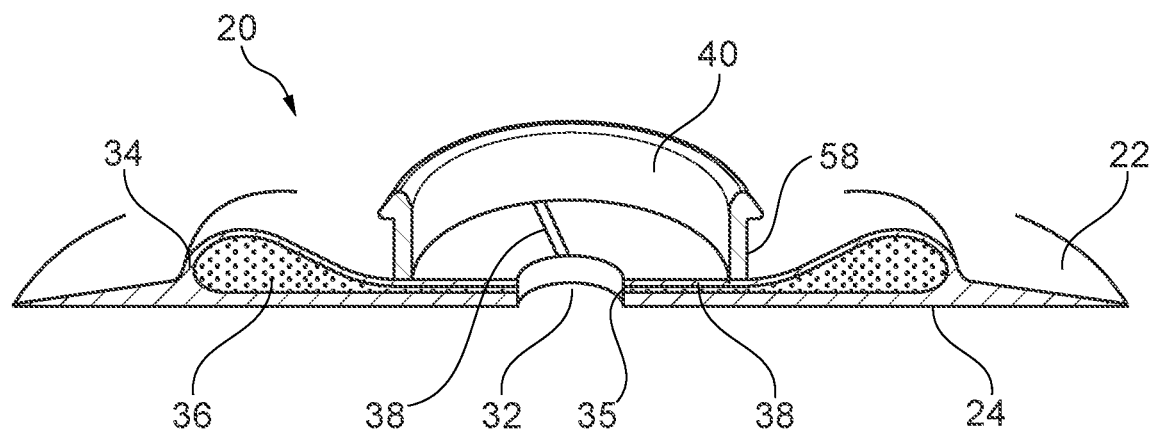
FIG. 14 is a schematic, cross-sectional view of one embodiment of a body side member comprising a first half of a coupling interface.
Figure 15:
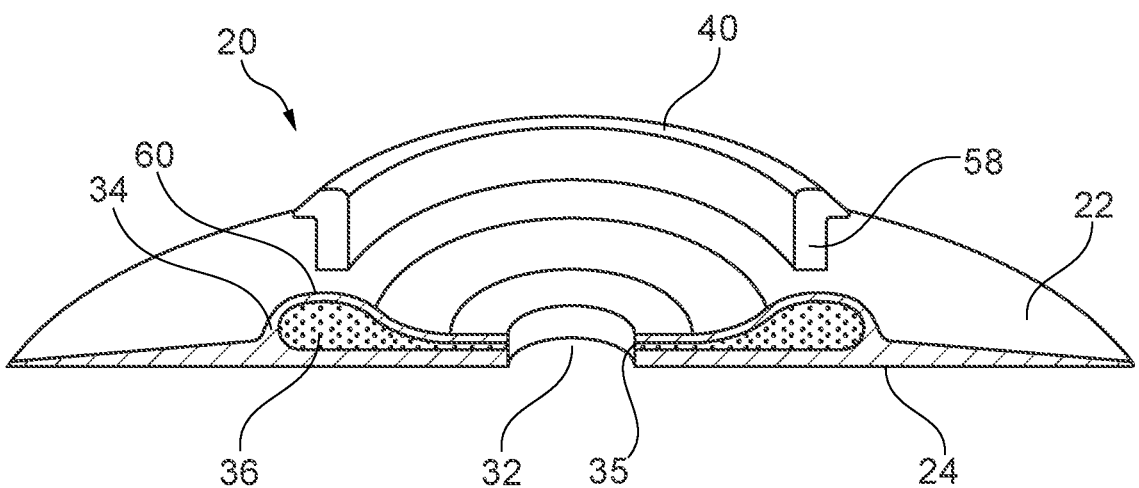
FIG. 15 is a schematic, cross-sectional view of one embodiment of a body side member comprising a first half of a coupling interface.
Figure 19:
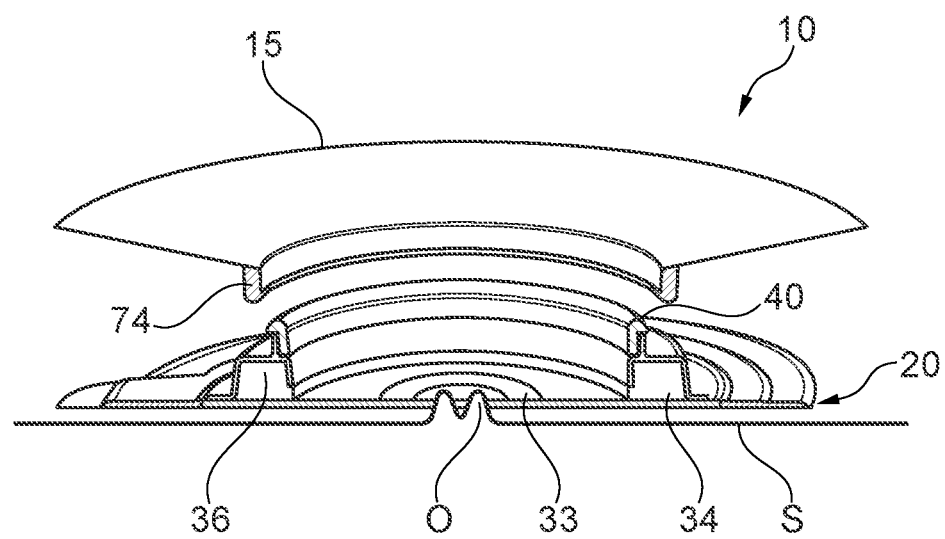
FIG. 19 is a schematic cross-sectional view of one embodiment of an ostomy appliance comprising a body side member attached to the skin surface of a user.

FIGS. 14 and 15 are schematic, cross-sectional views of embodiments of the body side member 20, wherein the distal surface 22 includes a first half 40 of a coupling interface for coupling the body side member 20 to a stomal output collecting bag (see FIG. 19).

In the embodiment of FIG. 14, the first coupling half 40 is an annular ring comprising an upstanding flange 58 protruding from and perpendicular to the distal surface 22 of the body side member 20. The flange 58 is configured for attaching a second coupling half 74 in the form of a coupling ring provided on a stomal output collecting bag 15 (FIG. 19). The first coupling half 40 is shown as being attached to the distal surface 22 of the body side member 20. In embodiments, the first coupling half 40 is attached to the distal surface 22 by an adhesive or by welding, but other ways of attaching are acceptable. As illustrated by way of example in FIG. 14, the first coupling half 40 is attached to the distal surface 22 at a location radially closer to the stoma-receiving opening 32 than where the pocket 34 is located. The body side member 20 of FIG. 14 further includes a channel 38 extending between a pocket 34 and the stoma-receiving opening 32. In FIG. 14, the pocket 34 is located radially outside of the annular first half of the coupling interface. This provides for the manipulable material 36 to be stored at a different location of the body side member 20 than where it may be needed and/or applied. In FIG. 14 the pocket 34 and thus the manipulable material 36 is located a distance from the stoma-receiving opening 32. The manipulable material 36 is configured to exit the pocket 34 through the opening 35.

In the embodiment of FIG. 15, the first half 40 of the coupling interface is attached to a distal-most portion 60 of the pocket 34. Thereby, pressure applied to the first half 40 and the second half 62 (FIG. 19), and in particular pressure applied when connecting a stomal output collecting bag 15 to the body side member 20, results in pressure forces being transferred by the first coupling half 40 onto the pocket 34 and to the manipulable material 36 inside the pocket, thereby causing manipulable material 36 to be dispensed from the pocket 34 via opening 35. In this manner, the act of coupling the body side member 20 and the stoma output collecting bag 15 to each other is advantageously combined with the act of dispensing the manipulable material 36 from the pocket 34.

Figure 16:
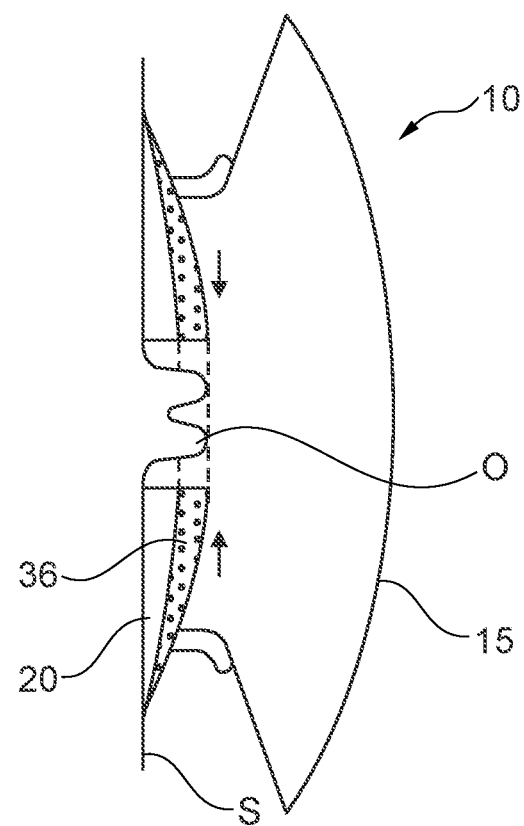
FIG. 16 is a schematic side view of one embodiment of an ostomy appliance comprising a body side member attached to the skin surface of a user.

FIG. 16 is a schematic cross-sectional view of one embodiment of an ostomy appliance 10 attached to the skin surface S around a stoma O of a user. In the embodiment of FIG. 16, one or more pockets 34 are provided "under" the first half 40 of the coupling interface, such that the first half 40 of the coupling interface is attached to a distal-most portion 60 of the pocket 34. A mass of manipulable material 36 is provided asymmetrically around the centre portion of the body side member 20. In FIG. 16 this is illustrated by a majority of the manipulable material 36 being located in one or more pockets 34, such that, in use of the appliance 10, the majority of the manipulable material 36 is available to be dispensed from the one or more pockets "below" the stoma O's protrusion from the skin surface S. This, and other asymmetrical configurations of the one or more pockets 34 and/or the manipulable material, provides for improved versatility in the distribution of manipulable material 36 on the body side member 20 and thus provides further options for individual customization according to the user's personal requirements.

Figure 17:
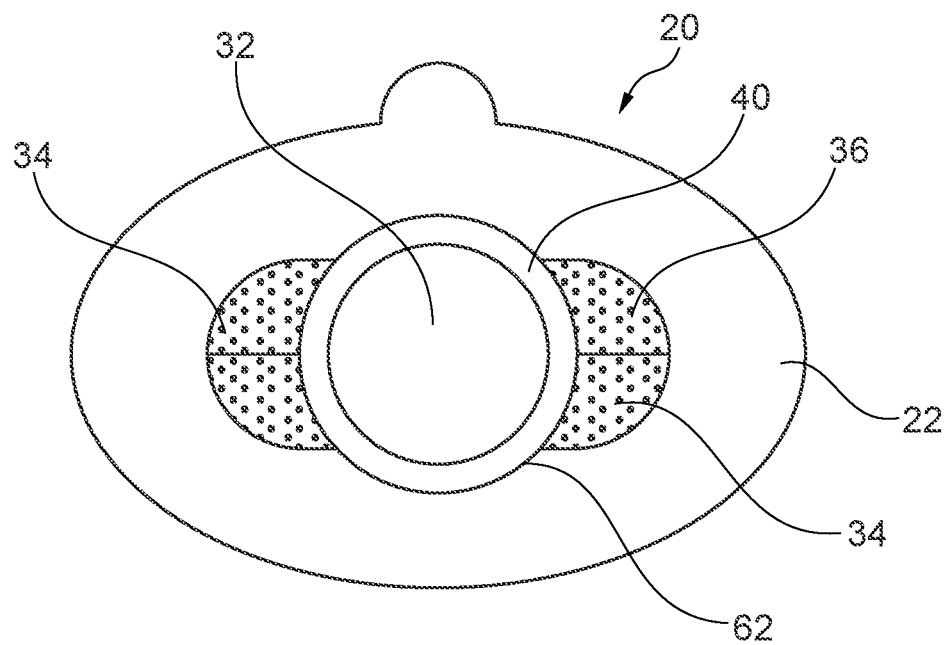
FIG. 17 is a schematic top view of one embodiment of a body side member.

FIG. 17 is a schematic top view of one embodiment of a body side member 20, wherein one or more pockets 34 are attached to the first half 40 of the coupling interface. In FIG. 17, the pockets 34 are attached to the first half 40 on or along a portion of an outer periphery 62 of the first half 40. Each of the pockets 34 contain a mass or volume of manipulable material 36. Instead of openings, the pockets 34 of the embodiment of FIG. 17 comprises a material which configures the pockets 34 to break or burst, when subjected to finger pressure, thereby allowing manipulable material 36 to be dispensed from the pockets 34. Particularly, the pockets 34 of FIG. 17 are formed as blister packages allowing for the pockets 34 to be closed until the manipulable material 36 is needed and to be individually activated by breaking the blister packages one at a time. One or more canals or openings (not shown) provide a passage for the manipulable material 36 between each of the pockets 34 and the distal surface 22 of the body side member 20, such that the manipulable material 36 can be externalized onto preferred locations on the distal surface 22.

Figure 18:
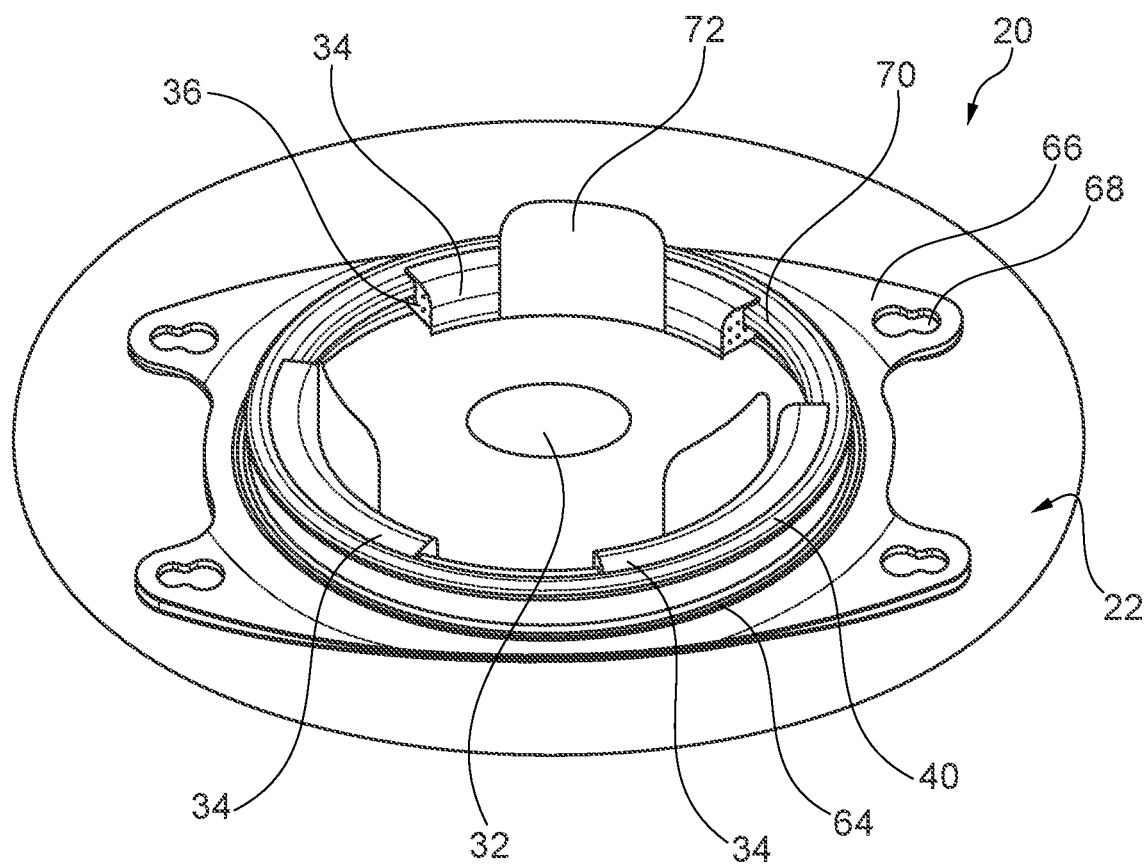
FIG. 18 is a schematic perspective view of one embodiment of a body side member.

FIG. 18 is a schematic perspective view of one embodiment of a body side member 20 comprising a first half 40 of a coupling interface, the first half 40 attached to the distal surface 22 of the body side member 20. In the embodiment shown in FIG. 18, the first half 40 is integrally formed with an attachment flange 64 extending substantially perpendicular to an upstanding flange 58 (FIG. 14) of the first half 40 of the coupling interface. The attachment flange 64 is shown comprising four protruding flanges forming sub-portions 66 of the attachment flange 64 and extending generally in the same plane as the attachment flange 64. A surface of the attachment flange 64 facing the distal surface 22 of the body side member 20 is suitable for attachment of the attachment flange 64 and thus the first half 40 of the coupling interface to the body side member 20. Each of the sub-portions 66 is illustrated comprising a connection opening 68. The connection opening 68 can be used to connect the body side member 20 to other components, such as, but not limited to, a belt (not shown) to help the user keeping the appliance safely attached to the body.

The embodiment of FIG. 18 further comprises one or more pockets 34 holding a manipulable material 36. The one or more pockets 34 is/are attached to an annular insert 70. The annular insert 70 is configured to fit in a snapping or clipping engagement with an inner periphery or portion of an annular ring of the first half 40 of the coupling interface. It is to be understood that the annular insert 70 may still be rotated within the annular ring of the first half 40 of the coupling interface after it has snapped or clipped into engagement therewith. This allows for additional control options in distributing the manipulable material 36 of a pocket 34 to the location where it is needed. In FIG. 18, three individual pockets 34 are shown, provided symmetrically around the centre portion of the body side member 20. Each of the pockets 34 can be open or closed pockets, as described above. In FIG. 18 the pockets 34 each have one opening facing towards the centre portion and the stoma receiving opening 32 of the body side member 20. However, the opening is not visible, since each opening is covered by a protective skirt 72. When the manipulable material 36 is needed, the user tears off one or more of the skirts 72 covering the opening of a respective pocket 34. This configuration allows for stepwise dispensing and thus exposure of the manipulable material 36 to moisture and stomal output, and the annular insert further allows for the pockets 34 to be rotated and located in a desired or preferred location on the distal surface 22 of the body side member 20.

FIG. 19 illustrates one embodiment of an ostomy appliance 10 including a body side member 20 as described herein and a stomal output collecting bag 15 configured to attached to the distal surface 22 of the body side member 20. In FIG. 19, the distal surface 22 of the body side member 20 comprises one single pocket 34. One single pocket should be interpreted to mean one and only one pocket 34. The single pocket 34 is configured to extend annularly around the centre portion 33 of the body side member 20. The single pocket 34 is attached to a first half 40 of a coupling interface for connection of the body side member 20 to a stomal output collecting bag 15. FIG. 19 shows one exemplary implementation of a connection between the single pocket 34 and the first half 40 of the coupling interface.

As illustrated in FIG. 19, the ostomy appliance 10 is a two-piece appliance including a coupling interface comprising a first half 40 and a second half 70 for connecting a stomal output collecting bag 15 to the body side member 20. It is to be understood that the ostomy appliance 10 may also be a one-piece ostomy appliance, i.e. without a coupling interface between the body side member 20 and the stomal output collecting bag 15.

Figure 20:
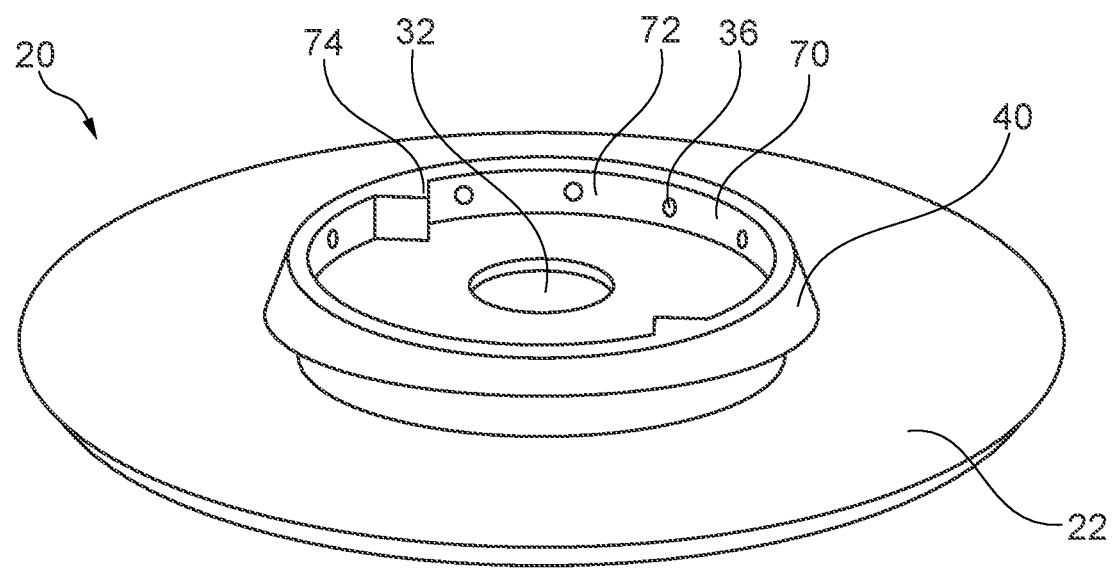
FIG. 20 is a schematic cross-sectional view of one embodiment of a body side member.

In the embodiment of FIG. 20, a first half 40 of the coupling interface comprises an inner annular ring (not shown) and an outer annular ring 70. An internal portion (not visible) of the outer annular ring 70 comprises alternating hollow and solid sections. The outer annular ring 70 receives the inner annular ring in the inner portion. The hollow sections of the outer annular ring 70 mate with loading sections of the inner annular ring containing manipulable material. A radially innermost wall 72 of the outer annular ring 70 comprises openings 36 coinciding with a hollow section of the outer annular ring 70. If the outer annular ring 70 and the inner annular ring are rotated in relation to each other, i.e. by turning on the outer annular ring 70, the solid internal sections of the outer annular ring forces manipulable material out of one or more the openings 36 onto that portion of the distal surface 22 of the body side member, which radially inside of the outer annular ring. The outer annular ring 70 includes one or more gripping portions 74 extending radially towards the stoma receiving opening 32 from the innermost wall 72. The gripping portions 74 are suitable for providing a firm grip on the outer annular ring 70 for turning it in relation to the inner annular ring and thus to dispense manipulable material out of the openings 36.

In another aspect of the disclosure, use of the body side member 20 for an ostomy appliance as disclosed herein for reducing the frequency of stomal output leakage incidents is contemplated. The advantageous effects provided by the embodiments of the body side member 20, aid in alleviating the nuisances of output leakages often encountered by users of ostomy appliances. This is at least partly achieved by the externalization of the manipulable material providing a better security against disintegration of the skin adhesive on the proximal surface of the backing film of the body side member. Use of the body side member according to the present disclosure allows for an increased wear time of an ostomy appliance.

Although specific embodiments have been illustrated and described herein, it will be appreciated by those of ordinary skill in the art that a variety of alternate and/or equivalent implementations may be substituted for the specific embodiments shown and described without departing from the scope of the present invention. This application is intended to cover any adaptations or variations of body side members for ostomy appliances as discussed herein. Therefore, it is intended that this invention be limited only by the claims and the equivalents thereof.

The invention claimed is:

1. A body side member of an ostomy appliance, the body side member comprising:
a proximal surface and a distal surface, at least a portion of the proximal surface comprising an adhesive;
a stoma receiving opening extending through the body side member; and
a layer of sheet material different from the adhesive, the layer of sheet material forms the distal surface of the body side member and is aqueously dissolvable;
wherein the layer of sheet material comprises one or more pockets, and each of the one or more pockets contains a manipulable material;
wherein, when the layer of sheet material dissolves, the manipulable material is movable relative to the adhesive between at least a first position inside the one or more pockets to a second position adapted to position the manipulable material to neutralize stomal output.

2. The body side member of claim 1, further comprising at least one opening formed in the one or more pockets, the opening providing a passage between an interior and an exterior of each of the one or more pockets for active dispensing of the manipulable material from the one or more pockets.

3. The body side member of claim 1, wherein the manipulable material comprises a neutralizing substance adapted to neutralize the stomal output, the neutralizing substance comprising one of a clay and a protease inhibitor.

4. The body side member of claim 1, wherein the manipulable material is movable out of the one or more pockets to a location distal of the body side member, such that manipulable material is available for engagement with stomal output.

5. The body side member of claim 1, further comprising a coupling interface attached to the distal surface of the body side member;
wherein the manipulable material is movable out of the one or more pockets over substantially an entirety of a portion of the distal surface of the body side member located radially within coupling interface.

6. The body side member of claim 1, wherein the layer of the sheet material is formed as a separate component and is removable and attachable to the body side member.

7. The body side member of claim 1, wherein the one or more pockets is formed between the layer of the sheet material and the adhesive.

8. The body side member of claim 1, wherein the stoma receiving opening is formed by an interior edge of the body side member, and the one or more pockets is provided with an opening communicating with the interior edge of the body side member.

9. The body side member of claim 1, wherein the one or more pockets is disposed between the stoma receiving opening and an outermost peripheral edge of the ostomy appliance, and an opening is formed on a radially outermost portion of the one or more pockets.

10. The body side member of claim 1, wherein an opening is provided in the one or more pockets, and the opening communicates with distalmost side of the body side member.

11. The body side member of claim 1 comprising a plurality of the one or more pockets, and wherein each pocket of the plurality of pockets comprises a plurality of openings.

12. The body side member of claim 1, wherein an opening is provided in the one or more pockets and the manipulable material is adapted to be dispensed from the opening.

13. The body side member of claim 1, wherein the one or more pockets each comprise at least two reservoir portions connected to each other by a transferring portion.

14. The body side member of claim 1, wherein the manipulable material comprises at least one of an adhesive, a powder, a liquid, a gel, a paste, a plurality of pellets or any combination thereof.

15. The body side member of claim 1, wherein the manipulable material is viscoelastic.

16. The body side member of claim 1, wherein the manipulable material is configured to swell in response to absorption of moisture.

17. The body side member of claim 1, wherein a wall of the one or more pockets comprises a thermoformable material.

18. The body side member of claim 1, further comprising a first half of a coupling interface for connection of an ostomy bag to the body side member, wherein the one or more pockets is attachable to the first half of the coupling interface.

19. The body side member of claim 18, wherein the first half of the coupling interface comprises a flange extending axially away from the distal surface of the body side member.

20. The body side member of claim 18, wherein the one or more pockets is disposed along an inner periphery of an annular insert, the annular insert is configured to engage with an annular ring of the first half of the coupling interface by snapping or clipping onto the annular ring, and thereby locate the annular insert radially closer to the central portion of the body side member than the annular ring.

21. The body side member of claim 1, wherein the manipulable material is movable inside the one or more pockets without the manipulable material moving external the pocket.

22. The body side member of claim 1, further comprising:
an ostomy bag attachable to the body side member.

* * * * *

UNITED STATES PATENT AND TRADEMARK OFFICE
CERTIFICATE OF CORRECTION

| | |
|---|---|
| PATENT NO. | : 11,491,043 B2 |
| APPLICATION NO. | : 16/498409 |
| DATED | : November 8, 2022 |
| INVENTOR(S) | : Langhorn et al. |

It is certified that error appears in the above-identified patent and that said Letters Patent is hereby corrected as shown below:

In the Specification

1. In Column 25, Line 52, delete "outer periphery 62" and insert -- outer periphery --, therefor.

2. In Column 26, Line 36, delete "open" and insert -- opened --, therefor.

3. In Column 26, Line 52, delete "attached" and insert -- attach --, therefor.

4. In Column 26, Line 65, delete "second half 70" and insert -- second half 62 --, therefor.

5. In Column 27, Line 13, delete "openings 36" and insert -- openings 35 --, therefor.

6. In Column 27, Line 18, delete "the openings 36" and insert -- of the openings 35 --, therefor.

7. In Column 27, Line 26, delete "openings 36." and insert -- openings 35. --, therefor.

Signed and Sealed this
Ninth Day of May, 2023

Katherine Kelly Vidal
*Director of the United States Patent and Trademark Office*